United States Patent
Yoshimura et al.

(10) Patent No.: US 7,301,705 B2
(45) Date of Patent: Nov. 27, 2007

(54) ALICYCLIC COMPOUND FOR OPTICAL MATERIAL

(75) Inventors: Yuichi Yoshimura, Mie (JP); Motoharu Takeuchi, Tokyo (JP); Teruo Kamura, Tokyo (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 355 days.

(21) Appl. No.: 10/474,704

(22) PCT Filed: Jun. 11, 2002

(86) PCT No.: PCT/JP02/05800

§ 371 (c)(1),
(2), (4) Date: Apr. 6, 2004

(87) PCT Pub. No.: WO02/102806

PCT Pub. Date: Dec. 27, 2002

(65) Prior Publication Data

US 2004/0158031 A1    Aug. 12, 2004

(30) Foreign Application Priority Data

Jun. 19, 2001   (JP)   ............... 2001-185491

(51) Int. Cl.
G02B 3/00      (2006.01)
G02B 5/00      (2006.01)
C07D 337/00    (2006.01)
C07D 335/00    (2006.01)
C08L 81/00     (2006.01)

(52) U.S. Cl. ............ 359/642; 252/582; 528/373; 525/535; 549/1; 549/9; 549/12; 549/13; 549/15; 549/16; 549/17; 549/20; 549/23; 549/26

(58) Field of Classification Search ............ None
See application file for complete search history.

(56) References Cited

U.S. PATENT DOCUMENTS 3,378,522 A      4/1968   Martin
6,201,061 B1 *   3/2001   Amagai et al. ............ 524/720

FOREIGN PATENT DOCUMENTS

| DE | 196 37 335 | 5/1997 |
| EP | 0 950 905 | 10/1999 |
| EP | 1398317 A1 * | 3/2004 |
| GB | 1121306 | 7/1968 |
| WO | WO 01/70853 | 9/2001 |

OTHER PUBLICATIONS

CAS# 96114-08-8 (Apr. 28, 1985).*
EPO Office action for application 02 733 473.9-2117, dated Mar. 3, 2007.*
International Search Report mailed Aug. 13, 2002 for PCT/JP02/05800.
J. Page, et al., "Visible-light Photochemistry and Phototoxicity of Thiarubines", Photochemistry and Photobiology, 1999, vol. 70, No. 2, pp. 159-165.
K. Steliou, et al., "Does Diatomic Sulfur ($S_2$) React as a Free Species?", J. Am. Chem. Soc., 1992, vol. 114, No. 4, pp. 1456-1462.
Hull, et al., "Thio-sugars. Part 8.[1] Methyl 2,3-Anhydro-5-thio-α-D-ribopyranoside and Methyl 3,4-Anhydro-5-thio-α-D-ribopyranoside", J. Chem. Soc., Perkin I, 1997, No. 10, pp. 1234-1239.

* cited by examiner

*Primary Examiner*—Michael J. Feely
(74) *Attorney, Agent, or Firm*—Antonelli, Terry, Stout & Kraus, LLP.

(57) ABSTRACT

The alicyclic compound of the present invention has a five- or more membered ring structure having an epithioethylene linkage and/or an epidithioethylene linkage, and has tow or more sulfur atoms in its molecule. Optical materials produced by curing the alicyclic compound or a composition containing the alicyclic compound by polymerization show high refractive index.

12 Claims, No Drawings

ALICYCLIC COMPOUND FOR OPTICAL MATERIAL

TECHNICAL FIELD

The present invention relates to optical materials suitable for producing plastic lenses, prisms, optical fibers, information recording media, and filters, particularly, suitable for producing plastic spectacle lenses.

BACKGROUND ART

Plastic materials have been widely used in various optical applications, particularly in manufacturing spectacle lenses, because of their lightweight, toughness and easiness of dyeing. Optical materials, particularly spectacle lenses are required to have, in addition to a low specific gravity, a high clearness, a low yellowness, and optical properties such as a high refractive index and a large Abbe's number. Since a large refractive index reduces the thickness of a lens, many studies have been made thereon to date and many novel compounds have been proposed. Recently, many organic compounds having sulfur atom and/or selenium atom have been proposed to achieve a high refractive index and a high Abbe's number. Of such compounds, some polyepisulfide compounds have been found to be well balanced in refractive index and Abbe's number. For example, Japanese Patent Application Laid-Open No. 9-110979 proposes a straight-chain polyepisulfide compound, Japanese Patent Application Laid-Open No. 9-71580 proposes a branched polyepisulfide compound, Japanese Patent Application Laid-Open No. 9-255781 proposes a polyepisulfide compound having a cyclic structure, and Japanese Patent Application Laid-Open No. 11-140046 proposes a polyepisulfide compound having selenium atom. However, the refractive index of materials obtained from these polyepisulfide are limited to 1.73 at most.

DISCLOSURE OF INVENTION

An object of the present invention is to provide an optical material which enables to attain a refractive index higher than attained by known materials.

As a result of extensive study for achieving the above object, the inventors have found that a five- or more membered alicyclic compound having an epithioethylene linkage and/or an epidithioethylene linkage in its ring structure and tow or more sulfur atoms in its molecule, or a composition containing the alicyclic compound provides an optical material having a high refractive index upon curing by polymerization.

BEST MODE FOR CARRYING OUT THE INVENTION

The alicyclic compound for use in the present invention has a five- or more membered ring structure which has at least one epithioethylene linkage and/or an epidithioethylene linkage (hereinafter referred to collectively as "epi(di)thioethylene linkage"). The alicyclic compound has two or more sulfur atoms including the sulfur atom in the epi(di)thioethylene linkage.

The optical material obtained by curing the alicyclic compound or a composition containing the alicyclic compound by polymerization exhibits a high refractive index. The composition may contain only one type or two or more of the alicyclic compounds. To achieve a high refractive index efficiently, the composition for optical materials contains the alicyclic compound in an amount preferably 5 to 100% by weight, more preferably 10 to 100% by weight based on the total amount thereof.

The composition for optical materials referred to herein may include a mixture comprising at least one type of the alicyclic compound as only one essential component and a mixture comprising at least one type of the alicyclic compound and a compound capable of reacting with the alicyclic compound (hereinafter referred to as "reactive compound") as the essential components. The reactive compound is not specifically limited as long as it provides a transparent resin usable as optical materials upon curing by polymerization with the alicyclic compound.

Examples of the alicyclic compound of the present invention include, but not limited to, 1,2-epidithiocyclopentane, 1,2-epidithiocyclohexane, 1,2:3,4-diepithiocyclopentane, 1,2:3,4-diepithiocyclohexane, 1,2:4,5-diepithiocyclohexane, 1,2:3,4:5,6-triepithiocyclohexane, 1,2:2,3:3,4:4,5:5,6:1,6-hexaepithiocyclohexane, 1,2-epithio-4-epithioethylcyclopentane, 1,2-epithio-3-epithioethylcyclohexane, 1,2-epithio-4-epithioethylcyclohexane, 1,2-epithio-3-thiacyclopentane, 1,2-epithio-4-thiacyclopentane, 1,2-epithio-3-thiacyclohexane, 1,2-epithio-4-thiacyclohexane, 1,2:4,5-diepithio-3-thiacyclohexane, 1,2:4,5-diepithio-3,6-dithiacyclohexane, 1,2:4,5-diepidithio-3,6-dithiacyclohexane, 1,2:4,5-diepithio-3,6,7-trithiacycloheptane, 1,2:5,6-diepithio-3,4,7,8-tetrathiacyclooctane, 1,2:5,6-diepidithio-3,4,7,8-tetrathiacyclooctane, 1,2:1,4:4,5-triepithio-3,6-dithiacyclohexane, 1,2:1,4:2,5:4,5-tetraepithio-3,6-dithiacyclohexane, and 1,2:1,4:2,5:4,5-tetraepidithio-3,6-dithiacyclohexane.

Of the above exemplified compounds, preferred are alicyclic compounds having at least one sulfide linkage in addition to the epi(di)thioethylene linkage in its ring structure or in its side chain, such as 1,2-epithio-4-epithioethylcyclopentane, 1,2-epithio-3-epithioethylcyclohexane, 1,2-epithio-4-epithioethylcyclohexane, 1,2-epithio-3-thiacyclopentane, 1,2-epithio-4-thiacyclopentane, 1,2-epithio-3-thiacyclohexane, 1,2-epithio-4-thiacyclohexane, 1,2:4,5-diepithio-3-thiacyclohexane, 1,2:4,5-diepithio-3,6-dithiacyclohexane, 1,2:4,5-diepidithio-3,6-dithiacyclohexane, 1,2:4,5-diepithio-3,6,7-trithiacycloheptane, 1,2:5,6-diepithio-3,4,7,8-tetrathiacyclooctane, 1,2:5,6-diepidithio-3,4,7,8-tetrathiacyclooctane, 1,2:1,4:4,5-triepithio-3,6-dithiacyclohexane, 1,2:1,4:2,5:4,5-tetraepithio-3,6-dithiacyclohexane, and 1,2:1,4:2,5:4,5-tetraepidithio-3,6-dithiacyclohexane.

More preferred are alicyclic compounds having two or more epi(di)thioethylene linkages, such as 1,2:4,5-diepithio-3-thiacyclohexane, 1,2:4,5-diepithio-3,6-dithiacyclohexane, 1,2:4,5-diepidithio-3,6-dithiacyclohexane, 1,2:4,5-diepithio-3,6,7-trithiacycloheptane, 1,2:5,6-diepithio-3,4,7,8-tetrathiacyclooctane, 1,2:5,6-diepidithio-3,4,7,8-tetrathiacyclooctane, 1,2:1,4:4,5-triepithio-3,6-dithiacyclohexane, 1,2:1,4:2,5:4,5-tetraepithio-3,6-dithiacyclohexane, and 1,2:1,4:2,5:4,5-tetraepidithio-3,6-dithiacyclohexane.

Still more preferred are alicyclic compounds represented by the following formula 1:

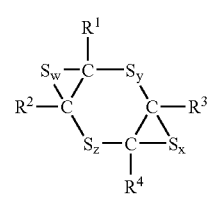

(1)

wherein S is sulfur atom; w and x are each independently 1 or 2; y and z are each independently integer from 0 to 2; $R^1$, $R^2$, $R^3$ and $R^4$ are each independently hydrogen or hydrocarbon group having 1 to 5 carbon atoms; excluding y and z being simultaneously zero. Examples of the alicyclic compounds represented by the formula 1 include 1,2:4,5-diepithio-3-thiacyclohexane, 1,2:4,5-diepithio-3,6-dithiacyclohexane, 1,2:4,5-diepidithio-3,6-dithiacyclohexane, 1,2:4,5-diepithio-3,6,7-trithiacycloheptane, 1,2:5,6-diepithio-3,4,7,8-tetrathiacyclooctane, and 1,2:5,6-diepidithio-3,4,7,8-tetrathiacyclooctane.

The alicyclic compounds may be synthesized mainly from corresponding olefins, epoxy compounds, dihalogenated compounds and dithiols by the following method:

(1) a method in which a cyclic olefin is reacted with a thiosulfenyl halide or disulfur dichloride, followed by ring closure with alkali treatment to produce a compound having an epithioethylene linkage, (2) a method in which a cyclic olefin is reacted with chlorosulfenylsuccinimide or chlorosulfenylphthalimide, followed by treatment with alkali metal halide to produce a compound having an epithioethylene linkage, (3) a method in which a cyclic olefin is reacted with a chlorothioacetic acid, followed by ring closure with hydrolysis to produce a compound having an epithioethylene linkage, (4) a method in which a cyclic epoxy compound is reacted with a thia-introducing agent such as alkali thiocyanate and thiourea to produce a compound having an epithioethylene linkage, (5) a method in which a cyclic gem-halogen compound is reacted with sodium sulfide to produce a compound having an epithioethylene linkage, (6) a method in which a cyclic gem-halogen compound is reacted with sodium disulfide to produce a compound having an epidithioethylene linkage, and (7) a method in which a cyclic gem-dithiol is subjected to hydrogenating ring closure in the presence of an oxidizing agent such as halogen and iron(III) chloride to produce a compound having an epidithioethylene linkage.

The above methods are only representative, and the alicyclic compound of the present invention may be synthesized by a combination of other known methods.

As described above, the composition for optical materials of the present invention may contain the reactive compound in addition to the alicyclic compound. The reactive compound is preferably an episulfide compound having a functional group that is easily reacted with the alicyclic compound, for example, an epithioethyl group and/or an epidithioethyl group represented by the following formula 2:

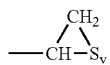

(2)

wherein S is sulfur atom and v is 1 or 2.

Examples of the episulfide compounds are shown below.

(1) Episulfide Compounds Having Aliphatic Chain Skeleton 1,1-Bis(epithioethyl)methane, 1-(epithioethyl)-1-(β-epithiopropyl)methane, 1,1-bis(β-epithiopropyl)methane, 1-(epithioethyl)-1-(β-epithiopropyl)ethane, 1,2-bis(β-epithiopropyl)ethane, 1-(epithioethyl)-3-(β-epithiopropyl)butane, 1,3-bis(β-epithiopropyl)propane, 1-(epithioethyl)-4-(β-epithiopropyl)pentane, 1,4-bis(β-epithiopropyl)butane, 1-(epithioethyl)-5-(β-epithiopropyl)hexane, 1-(epithioethyl)-2-(β-epithiobutylthio)ethane, 1-(epithioethyl)-2-[2-(β-epithiobutylthio)ethylthio]ethane, tetrakis(β-epithiopropyl)methane, 1,1,1-tris(β-epithiopropyl)propane, 1,3-bis(β-epithiopropyl)-1-(β-epithiopropyl)-2-thiapropane, 1,5-bis(β-epithiopropyl)-2,4-bis(β-epithiopropyl)-3-thiapentane, 1,3- or 1,4-bis(epithioethyl)cyclohexane, 1,3- or 1,4-bis(β-epithiopropyl)cyclohexane, bis[4-(epithioethyl)cyclohexyl]methane, bis[4-(β-epithiopropyl)cyclohexyl]methane, 2,2-bis[4-(epithioethyl)cyclohexyl]propane, 2,2-bis[4-(β-epithiopropyl)cyclohexyl]propane, bis[4-(β-epithiopropyl)cyclohexyl]sulfide, bis[4-(epithioethyl)cyclohexyl]sulfide, 2,5-bis(epithioethyl)-1,4-dithiane, 2,5-bis(β-epithiopropyl)-1,4-dithiane, 4-epithioethyl-1,2-cyclohexene sulfide, 4-epoxy-1,2-cyclohexene sulfide, 2,3-, 2,5- or 2,6-bis(1,2-epithioethyl)-1,4-diselenane, 2,3-, 2,5- or 2,6-bis(2,3-epithiopropyl)-1,4-diselenane, 2,4-, 2,5- or 2,6-bis(1,2-epithioethyl)-1,3-diselenane, 2,4-, 2,5- or 2,6-bis(2,4-epithiopropyl)-1,3-diselenane, 2,3-, 2,5-, 2,6- or 3,5-bis(1,2-epithioethyl)-1-thia-4-selenane, 2,3-, 2,5-, 2,6- or 3,5-bis(2,3-epithiopropyl)-1-thia-4-selenane, 2,4- or 4,5-bis(1,2-epithioethyl)-1,3-diselenolane, 2,4- or 4,5-bis(2,4-epithiopropyl)-1,3-diselenolane, 2,4-, 2,5- or 4,5-bis(1,2-epithioethyl)-1-thia-3-selenolane, 2,4-, 2,5- or 4,5-bis(2,4-epithiopropyl)-1-thia-3-selenolane, 2,3-, 2,4-, 2,5- or 3,4-bis(1,2-epithioethyl)selenophane, 2,3-, 2,4-, 2,5- or 3,4-bis(2,3-epithiopropyl)selenophane, 2,3-, 2,5- or 2,6-bis(1,2-epithioethyl)-1,4-ditellurane, 2,3-, 2,5- or 2,6-bis(2,3-epithiopropyl)-1,4-ditellurane, 2,4-, 2,5- or 2,6-bis(1,2-epithioethyl)-1,3-ditellurane, 2,4-, 2,5- or 2,6-bis(2,4-epithiopropyl)-1,3-ditellurane, 2,3-, 2,5-, 2,6- or 3,5-bis(1,2-epithioethyl)-1-thia-4-tellurane, 2,3-, 2,5-, 2,6- or 3,5-bis(2,3-epithiopropyl)-1-thia-4-tellurane, 2,4- or 4,5-bis(1,2-epithioethyl)-1,3-ditellurolane, 2,4- or 4,5-bis(2,4-epithiopropyl)-1,3-ditellurolane, 2,4-, 2,5- or 4,5-bis(1,2-epithioethyl)-1-thia-3-tellurolane, 2,4-, 2,5- or 4,5-bis(2,4-epithiopropyl)-1-thia-3-tellurolane, 2,3-, 2,4-, 2,5- or 3,4-bis(1,2-epithioethyl)tellurophane, 2,3-, 2,4-, 2,5- or 3,4-bis(2,3-epithiopropyl)tellurophane, 1,3- or 1,4-bis(epithioethyl)benzene, 1,3- or 1,4-bis(β-epithiopropyl)benzene, bis[4-(epithioethyl)phenyl]methane, bis[4-(β-epithiopropyl)phenyl]methane, 2,2-bis[4-(epithioethyl)phenyl]propane, 2,2-bis[4-(β-epithiopropyl)phenyl]propane, bis[4-(epithioethyl)phenyl]sulfide, bis[4-(β-epithiopropyl)phenyl]sulfide, bis[4-(epithioethyl)phenyl]sulfone, bis[4-(β-epithiopropyl)phenyl]sulfone, 4,4'-bis(epithioethyl)biphenyl, and 4,4'-bis(β-epithiopropyl)biphenyl.

(2) Thioglycidyl Ethers

Methyl thioglycidyl ether, ethyl thioglycidyl ether, propyl thioglycidyl ether, and butyl thioglycidyl ether.

(3) Episulfide Compounds Having at Least one epithioalkyloxy Group

Bis(β-epithiopropyl)ether, bis(β-epithiopropyloxy)methane, 1,2-bis(β-epithiopropyloxy)ethane, 1,3-bis(β-epithiopropyloxy)propane, 1,2-bis(β-epithiopropyloxy)propane, 1-(β-epithiopropyloxy)-2-(β-epithiopropyloxymethyl)propane, 1,4-bis(β-epithiopropyloxy)butane, 1,3-bis(β-epithiopropyloxy)butane, 1-(β-epithiopropyloxy)-3-(β-epithiopropyloxymethyl)butane, 1,5-bis(β-epithiopropyloxy)pentane, 1-(β-epithiopropyloxy)-4-(β-epithiopropyloxymethyl)pentane, 1,6-bis(β-epithiopropyloxy)hexane, 1-(β-epithiopropyloxy)-5-(β-epithiopropyloxymethyl)hexane, 1-(β-epithiopropyloxy)-2-[(2-β-epithiopropyloxyethyl)oxy]ethane, 1-(β-epithiopropyloxy)-2-[[2-(2-β-epithiopropyloxyethyl)

oxyethyl]oxy]ethane, bis(5,6-epithio-3-oxahexyl) selenide, bis(5,6-epithio-3-oxahexyl) telluride, tetrakis(β-epithiopyloxymethyl)methane, 1,1,1-tris(β-epithiopropyloxymethyl)propane, 1,5-bis(β-epithiopropyloxy)-2-(β-epithiopropyloxymethyl)-3-thiapentane, 1,5-bis(β-epithiopropyloxy)-2,4-bis(β-epithiopropyloxymethyl)-3-thiapentane, 1-(β-epithiopropyloxy)-2,2-bis(β-epithiopropyloxymethyl)-4-thiahexane, 1,5,6-tris(β-epithiopropyloxy)-4-(β-epithiopropyloxymethyl)-3-thiahexane, 1,8-bis(β-epithiopropyloxy)-4-(β-epithiopropyloxymethyl)-3,6-dithiaoctane, 1,8-bis(β-epithiopropyloxy)-4,5bis(β-epithiopropyloxymethyl)-3,6-dithiaoctane, 1,8-bis(β-epithiopropyloxy)-4,4-bis(β-epithiopropyloxymethyl)-3,6-dithiaoctane, 1,8-bis(β-epithiopropyloxy)-2,4,5-bis(β-epithiopropyloxymethyl)-3,6-dithiaoctane, 1,8-bis(β-epithiopropyloxy)-2,5-bis(β-epithiopropyloxymethyl)-3,6-dithiaoctane, 1,9-bis(β-epithiopropyloxy)-5-(β-epithiopropyloxymethyl)-5-[(2-β-epithiopropyloxyethyl)oxymethyl]-3,7-dithianonane, 1,10-bis(β-epithiopropyloxy)-5,6-bis[(2β-epithiopropyloxyethyl)oxy]-3,6,9-trithiadecane, 1,11-bis(β-epithiopropyloxy)-4,8-bis(β-epithiopropyloxymethyl)-3,6,9-trithiaundecane, 1,11-bis(β-epithiopropyloxy)-5,7-bis(β-epithiopropyloxymethyl)-3,6,9-trithiaundecane, 1,11-bis(β-epithiopropyloxy)-5,7-[(2-β-epithiopropyloxyethyl)oxymethyl]-3,6,9-trithiaundecane, 1,11-bis(β-epithiopropyloxy)-4,7-bis(β-epithiopropyloxymethyl)-3,6,9-trithiaundecane, 1,3- or 1,4-bis(β-epithiopropyloxy)cyclohexane, 1,3- or 1,4-bis(β-epithiopropyloxymethyl)cyclohexane, bis[4-(β-epithiopropyloxy)cyclohexyl]methane, 2,2-bis[4-(β-epithiopropyloxy)cyclohexyl]propane, bis[4-(β-epithiopropyloxy)cyclohexyl]sulfide, 2,5-bis(β-epithiopropyloxymethyl)-1,4-dithiane, 2,5-bis(β-epithiopropyloxyethyloxymethyl)-1,4-dithiane, 2,4- or 4,5-bis(3,4-epithio-1-oxabutyl)-1,3-diselenolane, 2,4- or 4,5-bis(4,5-epithio-2-oxapentyl)-1,3-diselenolane, 2,4-, 2,5- or 4,5-bis(3,4-epithio-1-oxabutyl)-1-thia-3-selenolane, 2,4-, 2,5- or 4,5-bis(4,5-epithio-2-oxapentyl)-1-thia-3-selenolane, bis(3,4-epithio-1-oxabutyl)tricycloselenaoctane, bis(3,4-epithio-1-oxabutyl)dicycloselenanonane, 2,3-, 2,4-, 2,5- or 3,4-bis(3,4-epithio-1-oxabutyl)selenophane, 2,3-, 2,4-, 2,5- or 3,4-bis(4,5-epithio-2-oxapentyl)selenophane, 2,3-, 2,5- or 2,6-bis(3,4-epithio-1-oxabutyl)-1,4-diselenane, 2,3-, 2,5- or 2,6-bis(4,5-epithio-2-oxapentyl)-1,4-diselenane, 2,4-, 2,5- or 2,6-bis(3,4-epithio-1-oxabutyl)-1,3-diselenane, 2,4-, 2,5- or 2,6-bis(4,5-epithio-2-oxapentyl)-1,3-diselenane, 2,3-, 2,5-, 2,6- or 3,5-bis(3,4-epithio-1-oxabutyl)-1-thia-4-selenane, 2,3-, 2,5-, 2,6- or 3,5-bis(4,5-epithio-2-oxapentyl)-1-thia-4-selenane, 2,4- or 4,5-bis(3,4-epithio-1-oxabutyl-1,3-ditellurolane, 2,4- or 4,5-bis(4,5-epithio-2-oxapentyl)-1,3-ditellurolane, 2,4-, 2,5- or 4,5-bis(3,4-epithio-1-oxabutyl)-1-thia-3-tellurolane, 2,4-, 2,5- or 4,5-bis(4,5-epithio-2-oxapentyl)-1-thia-3-tellurolane, bis(3,4-epithio-1-oxabutyl)tricyclotelluraoctane, bis(3,4-epithio-1-oxabutyl)dicycloteluranonane, 2,3-, 2,4-, 2,5- or 3,4-bis(3,4-epithio-1-oxabutyl)tellurophane, 2,3-, 2,4-, 2,5- or 3,4-bis(4,5-epithio-2-oxapentyl)tellurophane, 2,3-, 2,5- or 2,6-bis(3,4-epithio-1-oxabutyl)-1,4-ditellurane, 2,3-, 2,5- or 2,6-bis(4,5-epithio-2-oxapentyl)-1,4-ditellurane, 2,4-, 2,5- or 2,6-bis(3,4-epithio-1-oxabutyl)-1,3-ditellurane, 2,4-, 2,5- or 2,6-bis(4,5-epithio-2-oxapentyl)-1,3-ditellurane, 2,3-, 2,5-, 2,6- or 3,5-bis(3,4-epithio-1-oxabutyl)-1-thia-4-tellurane, 2,3-, 2,5-, 2,6- or 3,5-bis(4,5-epithio-2-oxapentyl)-1-thia-4-tellurane, 1,3- or 1,4-bis(β-epithiopropyloxy)benzene, 1,3- or 1,4-bis(β-epithiopropyloxymethyl)benzene, bis[4-(β-epithiopropyl)phenyl]methane, 2,2-bis[4-(β-epithiopropylthio)phenyl]propane, bis[4-(β-epithiopropylthio)phenyl]sulfide, bis[4-(β-epithiopropylthio)phenyl]sulfone, and 4,4'-bis(β-epithiopropylthio)biphenyl.

(4) Episulfide Compounds Having at Least One Epithioalkylthio Group

Bis(epithioethyl)sulfide, bis(epithioethyl)disulfide, bis(β-epithiopropyl)sulfide, bis(β-epithiopropyl)disulfide, bis(β-epithiopropyl)trisulfide, bis(β-epithiopropylthio)methane, 1,2-bis(β-epithiopropylthio)ethane, 1,3-bis(β-epithiopropylthio)propane, 1,2-bis(β-epithiopropylthio)propane, 1-(β-epithiopropylthio)-2-(β-epithiopropylthiomethyl)propane, 1,4-bis(β-epithiopropylthio)butane, 1,3-bis(β-epithiopropylthio)butane, 1-(β-epithiopropylthio)-3-(β-epithiopropylthiomethyl)butane, 1,5-bis(β-epithiopropylthio)pentane, 1-(β-epithiopropylthio)-4-(β-epithiopropylthiomethyl)pentane, 1,6-bis(β-epithiopropylthio)hexane, 1-(β-epithiopropylthio)-5-(β-epithiopropylthiomethyl)hexane, 1-(β-epithiopropylthio)-2-[(2-β-epithiopropylthioethyl)thio]ethane, 1-(β-epithiopropylthio)-2-[[2-(2-β-epithiopropylthioethyl)thioethyl]thio]ethane, tetrakis(β-epithiopropylthiomethyl)methane, 1,1,1-tris(β-epithiopropylthiomethyl)-3-thiapentane, 1,5-bis(β-epithiopropylthio)-2,4-bis(β-epithiopropylthiomethyl)-3-thiapentane, 1-(β-epithiopropylthio)-2,2-bis(β-epithiopropylthiomethyl)-4-thiahexane, 1,5,6-tris(β-epithiopropylthio)-4-(β-epithiopropylthiomethyl)-3-thiahexane, 1,8-bis(β-epithiopropylthio)-4-(β-epithiopropylthiomethyl)-3,6-dithiaoctane, 1,8-bis(β-epithiopropylthio)-4,5bis(β-epithiopropylthiomethyl)-3,6-dithiaoctane, 1,8-bis(β-epithiopropylthio)-4,4-bis(β-epithiopropylthiomethyl)-3,6-dithiaoctane, 1,8-bis(β-epithiopropylthio)-2,4,5-tris(β-epithiopropylthiomethyl)-3,6-dithiaoctane, 1,8-bis(β-epithiopropylthio)-2,5-bis(β-epithiopropylthiomethyl)-3,6-dithiaoctane, 1,9-bis(β-epithiopropylthio)-5-(β-epithiopropylthiomethyl)-5-[(2-β-epithiopropylthioethyl)thiomethyl]-3,7-dithianonane, 1,10-bis(β-epithiopropylthio)-5,6-bis[(2-β-epithiopropylthioethyl)thio]-3,6,9-trithiadecane, 1,11-bis(β-epithiopropylthio)-4,8-bis(β-epithiopropylthiomethyl)-3,6,9-trithiaundecane, 1,11-bis(β-epithiopropylthio)-5,7-bis(β-epithiopropylthiomethyl)-3,6,9-trithiaundecane, 1,11-bis(β-epithiopropylthio)-5,7-[(2-β-epithiopropylthioethyl)thiomethyl]-3,6,9-trithiaundecane, 1,11-bis(β-epithiopropylthio)-4,7-bis(β-epithiopropylthiomethyl)-3,6,9-trithiaundecane, tetra[2-(β-epithiopropylthio)acetylmethyl]methane, 1,1,1-tri[2-(β-epithiopropylthio)acetylmethyl]propane, tetra[2-(β-epithiopropylthiomethyl)acetylmethyl]methane, 1,1,1-tri[2-(β-epithiopropylthiomethyl)acetylmethyl]propane, bis(5,6-epithio-3-thiahexyl) selenide, 2,3-bis(6,7-thioepoxy-1-selena-4-thiaheptyl)-1-(3,4-thioepoxy-1-thiabutyl)propane, 1,1,3,3-tetrakis(4,5-thioepoxy-2-thiapentyl)-2-selenapropane, bis(4,5-thioepoxy-2-thiapentyl)-3,6,9-triselenaundecane-1,11-bis(3,4-thioepoxy-1-thiabutyl), 1,4-bis(3,4-thioepoxy-1-thiabutyl)-2,3-bis(6,7-thioepoxy-1-selena-4-thiaheptyl)butane, tris(4,5-thioepoxy-2-thiapentyl)-3-selena-6-thiaoctane-1,8-bis(3,4-thioepoxy-1-thiabutyl), bis(5,6-epithio-3-thiahexyl) telluride, 2,3-bis(6,7-thioepoxy-1-tellura-4-thiaheptyl)-1-(3,4-thioepoxy-1-thiabutyl)propane, 1,1,3,3,-tetrakis(4,5-thioepoxy-2-thiapentyl)-2-tellurapropane, bis(4,5-thioepoxy-2-thiapentyl)-3,6,9-tritelluraundecane-1,11-bis(3,4-thioepoxy-1-thiabutyl), 1,4-bis(3,4-thioepoxy-1-thiabutyl)-2,3-bis(6,7-thioepoxy-1-tellura-4-thiaheptyl)butane, tris(4,5-thioepoxy-2-thiapentyl)-3-tellura-6-thiaoctane-1,8-bis(3,4-thioepoxy-1-thiabutyl), 1,3- or 1,4-bis(β-epithiopropylthio)cyclohexane, 1,3- or 1,4-bis (β-epithiopropylthiomethyl)cyclohexane, bis[4-(β-epithiopropylthio)cyclohexyl]methane, 2,2-bis[4-(β-epithiopropylthio)cyclohexyl]propane, bis[4-(β-epithiopropylthio)cyclohexyl]sulfide, 2,5-bis(β-epithiopropylthiomethyl)-1,4-dithiane, 2,5-bis(β-epithiopropylthioethylthiomethyl)-1,4-dithiane, 2,3-, 2,5- or 2,6-bis(3,4-epithio-1-thiabutyl)-1,4-diselenane, 2,3-, 2,5- or 2,6-bis(4,5-epithio-2-thiapentyl)-1,4-diselenane, 2,4-, 2,5- or 5,6-bis(3,4-epithio-1-thiabutyl)-1,3-diselenane, 2,4-, 2,5- or 5,6-bis(4,5-epithio-2-thiapentyl)-1,3-diselenane, 2,3-, 2,5-, 2,6- or 3,5-bis(3,4-epithio-1-thiabutyl)-1-thia-4-selenane, 2,3-, 2,5-, 2,6- or 3,5-bis(4,5-epithio-2-thiapentyl)-1-thia-4-selenane, 2,4- or 4,5-bis(3,4-epithio-1-thiabutyl)-1,3-diselenolane, 2,4- or 4,5-bis(4,5-epithio-2-thiapentyl)-1,3-diselenolane, 2,4-, 2,5- or 4,5-bis(3,4-epithio-1-thiabutyl)-1-thia-3-selenolane, 2,4-, 2,5- or 4,5-bis(4,5-epithio-2-thiapentyl)-1-thia-3-selenolane, 2,6-bis(4,5-epithio-2-thiapentyl-1,3,5-triselenane, bis(3,4-epithio-1-thiabutyl)tricycloselenaoctane, bis(3,4-epithio-1-thiabutyldicycloselenanonane, 2,3-, 2,4-, 2,5- or 3,4-bis(3,4-epithio-1-thiabutyl)selenophane, 2,3-, 2,4-, 2,5- or 3,4-bis(4,5-epithio-2-thiapentyl)selenophane, 2-(4,5-thioepoxy-2-thiapentyl)-5-(3,4-thioepoxy-1-thiabutyl)-1-selenacyclohexane, 2,3-, 2,4-, 2,5-, 2,6-, 3,4-, 3,5- or 4,5-bis(3,4-thioepoxy-1-thiabutyl)-1-selenacyclohexane, 2,3-, 2,4-, 2,5-, 2,6-, 3,4-, 3,5- or 4,5-bis(4,5-thioepoxy-2-thiapentyl)-1-selenacyclohexane, 2,3-, 2,5- or 2,6-bis(3,4-epithio-1-thiabutyl)-1,4-ditellurane, 2,3-, 2,5- or 2,6-bis(4,5-epithio-2-thiapentyl)-1,4-ditellurane, 2,4-, 2,5- or 5,6-bis(3,4-epithio-1-thiabutyl)-1,3-ditellurane, 2,4-, 2,5- or 5,6-bis(4,5-epithio-2-thiapentyl)-1,3-ditellurane, 2,3-, 2,5-, 2,6- or 3,5-bis(3,4-epithio-1-thiabutyl)-1-thia-4-tellurane, 2,3-, 2,5-, 2,6- or 3,5-bis(4,5-epithio-2-thiapentyl)-1-thia-4-tellurane, 2,4- or 4,5-bis(3,4-epithio-1-thiabutyl)-1,3-ditellurolane, 2,4- or 4,5-bis(4,5-epithio-2-thiapentyl)-1,3-ditellurolane, 2,4-, 2,5- or 4,5-bis(3,4-epithio-1-thiabutyl)-1-thia-3-tellurolane, 2,4-, 2,5- or 4,5-bis(4,5-epithio-2-thiapentyl)-1-thia-3-tellurolane, 2,6-bis(4,5-epithio-2-thiapentyl-1,3,5-tritellurane, bis(3,4-epithio-1-thiabutyltricyclotelluraoctane, bis(3,4-epithio-1-thiabutyl)dicyclotelluranonane, 2,3-, 2,4-, 2,5- or 3,4-bis(3,4-epithio-1-thiabutyl)tellurophane, 2,3-, 2,4-, 2,5- or 3,4-bis(4,5-epithio-2-thiapentyl)tellurophane, 2-(4,5-thioepoxy-2-thiapentyl)-5-(3,4-thioepoxy-1-thiabutyl)-1-telluracyclohexane, 2,3-, 2,4-, 2,5-, 2,6-, 3,4-, 3,5- or 4,5-bis(3,4-thioepoxy-1-thiabutyl)-1-telluracyclohexane, 2,3-, 2,4-, 2,5-, 2,6-, 3,4-, 3,5- or 4,5-bis(4,5-thioepoxy-2-thiapentyl)-1-telluracyclohexane, 1,3- or 1,4-bis(β-epithiopropylthio)benzene, 1,3- or 1,4-bis(β-epithiopropylthiomethyl)benzene, bis[4-(β-epithiopropylthio)phenyl]methane, 2,2-bis[4-(β-epithiopropylthio)phenyl]propane, bis[4-(β-epithiopropylthio)phenyl]sulfide, bis[4-(β-epithiopropylthio)phenyl]sulfone, and 4,4'-bis(β-epithiopropylthio)biphenyl.

(5) Episulfide Compounds Having at Least One Epithioalkylseleno Group

Bis(β-epithiopropyl) selenide, bis(β-epithiopropyl) diselenide, bis(β-epithiopropyl)tri selenide, bis(β-epithiopropylseleno)methane, 1,2-bis(β-epithiopropylseleno)ethane, 1,3-bis(β-epithiopropylseleno)propane, 1,2-bis(β-epithiopropylseleno)propane, 1-(β-epithiopropylseleno)-2-(β-epithiopropylselenomethyl)propane, 1,4-bis(β-epithiopropylseleno)butane, 1,3-bis(β-epithiopropylseleno)butane, 1-(β-epithiopropylseleno)-3-(β-epithiopropylselenomethyl)butane, 1,5-bis(β-epithiopropylseleno)pentane, 1-(β-epithiopropylseleno)-4-(β-epithiopropylselenomethyl)pentane, 1,6-bis(β-epithiopropylseleno)hexane, 1-(β-epithiopropylseleno)-5-(β-epithiopropylselenomethyl)hexane, 1-(β-epithiopropylseleno)-2-[(2-β-epithiopropylselenoethyl)thio]ethane, 1-(β-epithiopropylseleno)-2-[[2-(2-β-epithiopropylselenoethyl)selenoethyl]thio]ethane, tetrakis(β-epithiopropylselenomethyl)methane, 1,1,1-tris(β-epithiopropylselenomethyl)propane, 1,5-bis(β-epithiopropylseleno)-2,4-bis(β-epithiopropylselenomethyl)-3-thiapentane, 1-(β-epithiopropylseleno)-2,2-bis(β-epithiopropylselenomethyl)-4-thiahexane, 1,5,6-tris(β-epithiopropylseleno)-4-(β-epithiopropylselenomethyl)-3-thiahexane, 1,8-bis(β-epithiopropylseleno)-4-(β-epithiopropylselenomethyl)-3,6-dithiaoctane, 1,8-bis(β-epithiopropylseleno)-4,5bis(β-epithiopropylselenomethyl)-3,6-dithiaoctane, 1,8-bis(β-epithiopropylseleno)-4,4-bis(β-epithiopropylselenomethyl)-3,6-dithiaoctane, 1,8-bis(β-epithiopropylseleno)-2,4,5-tris(β-epithiopropylselenomethyl)-3,6-dithiaoctane, 1,8-bis(β-epithiopropylseleno)-2,5-bis(β-epithiopropylselenomethyl)-3,6-dithiaoctane, 1,9-bis(β-epithiopropylseleno)-5-(β-epithiopropylselenomethyl)-5-[(2-β-epithiopropylselenoethyl)selenomethyl]-3,7-dithianonane, 1,10-bis(β-epithiopropylseleno)-5,6-bis[(2-β-epithiopropylselenoethyl)thio]-3,6,9-trithiadecane, 1,11-bis(β-epithiopropylseleno)-4,8-bis(β-epithiopropylselenomethyl)-3,6,9-trithiaundecane, 1,11-bis(β-epithiopropylseleno)-5,7-bis(β-epithiopropylselenomethyl)-3,6,9-trithiaundecane, 1,11-bis(β-epithiopropylseleno)-5,7-[(2-β-epithiopropylselenoethyl)selenomethyl]-3,6,9-trithiaundecane, 1,11-bis(β-epithiopropylseleno)-4,7-bis(β-epithiopropylselenomethyl)-3,6,9-trithiaundecane, tetra[2-(β-epithiopropylseleno)acetylmethyl]methane, 1,1,1-tri[2-(β-epithiopropylseleno)acetylmethyl]propane, tetra[2-(β-epithiopropylselenomethyl)acetylmethyl]methane, 1,1,1-tri[2-(β-epithiopropylselenomethyl)acetylmethyl]propane, bis(5,6-epithio-3-selenohexyl) selenide, 2,3-bis(6,7-thioepoxy-1-selena-4-selenoheptyl)-1-(3,4-thioepoxy-1-selenobutyl)propane, 1,1,3,3-tetrakis(4,5-thioepoxy-2-selenopentyl)-2-selenapropane, bis(4,5-thioepoxy-2-selenopentyl)-3,6,9-triselenaundecane-1,11-bis(3,4-thioepoxy-1-selenobutyl), 1,4-bis(3,4-thioepoxy-1-selenobutyl)-2,3-bis(6,7-thioepoxy-1-selena-4-selenoheptyl)butane, tris(4,5-thioepoxy-2-selenopentyl)-3-selena-6-thiaoctane-1,8-bis(3,4-thioepoxy-1-selenobutyl), bis(5,6-epithio-3-selenohexyl) telluride, 2,3-bis(6,7-thioepoxy-1-tellura-4-selenoheptyl)-1-(3,4-thioepoxy-1-selenobutyl)propane, 1,1,3,3,-tetrakis(4,5-thioepoxy-2-selenopentyl)-2-tellurapropane, bis(4,5-thioepoxy-2-selenopentyl)-3,6,9-tritelluraundecane-1,11-bis(3,4-thioepoxy-1-selenobutyl), 1,4-bis(3,4-thioepoxy-1-selenobutyl)-2,3-bis(6,7-thioepoxy-1-tellura-4-selenoheptyl)butane, tris(4,5-thioepoxy-2-selenopentyl)-3-tellura-6-thiaoctane-1,8-bis(3,4-thioepoxy-1-selenobutyl), 1,3- or 1,4-bis(β-epithiopropylseleno)cyclohexane, 1,3- or 1,4-bis(β-epithiopropylselenomethyl)cyclohexane, bis[4-(β-epithiopropylseleno)cyclohexyl]methane, 2,2-bis[4-(β-epithiopropylseleno)cyclohexyl]propane, bis[4-(β-epithiopropylseleno)cyclohexyl]sulfide, 2,5-bis(β-epithiopropylselenomethyl)-1,4-dithiane, 2,5-bis(β-epithiopropylselenoethylthiomethyl)-1,4-dithiane, 2,3-, 2,5- or 2,6-bis(3,4-epithio-1-selenobutyl)-1,4-diselenane, 2,3-, 2,5- or 2,6-bis(4,5-epithio-2-selenopentyl)-1,4-diselenane, 2,4-, 2,5- or 5,6-bis(3,4-epithio-1-selenobutyl)-1,3-diselenane, 2,4-, 2,5- or 5,6-bis(4,5-epithio-2-selenopentyl)-1,3-diselenane, 2,3-, 2,5-, 2,6- or 3,5-bis(3,4-epithio-1-selenobutyl)-1-thia-4-selenane, 2,3-, 2,5-, 2,6- or 3,5-bis(4,5-epithio-2-selenopentyl)-1-thia-4-selenane, 2,4- or 4,5-bis(3,4-epithio-1-selenobutyl)-1,3-diselenolane, 2,4- or 4,5-bis(4,5-epithio-2-selenopentyl)-1,3-diselenolane, 2,4-, 2,5- or 4,5-bis(3,4-epithio-1-selenobutyl)-1-thia-3-selenolane, 2,4-, 2,5- or 4,5-bis(4,5-epithio-2-selenopentyl)-1-thia-3-selenolane, 2,6-bis(4,5-epithio-2-selenopentyl-1,3,5-triselenane, bis(3,4-epithio-1-selenobutyl)tricycloselenaoctane, bis(3,4-epithio-1-selenobutyl)dicycloselenanonane, 2,3-, 2,4-, 2,5- or 3,4-bis(3,4-epithio-1-selenobutyl)selenophane, 2,3-, 2,4-, 2,5- or 3,4-bis(4,5-epithio-2-selenopentyl)selenophane, 2-(4,5-thioepoxy-2-selenopentyl)-5-(3,4-thioepoxy-1-selenobutyl)-1-selenacyclohexane, 2,3-, 2,4-, 2,5-, 2,6-, 3,4-, 3,5- or 4,5-bis(3,4-thioepoxy-1-selenobutyl)-1-selenacyclohexane, 2,3-, 2,4-, 2,5-, 2,6-, 3,4-, 3,5- or 4,5-bis(4,5-thioepoxy-2-selenopentyl)-1-selenacyclohexane, 2,3-, 2,5- or 2,6-bis(3,4-epithio-1-selenobutyl)-1,4-ditellurane, 2,3-, 2,5- or 2,6-bis(4,5-epithio-2-selenopentyl)-1,4-ditellurane, 2,4-, 2,5- or 5,6-bis(3,4-epithio-1-selenobutyl)-1,3-ditellurane, 2,4-, 2,5- or 5,6-bis(4,5-epithio-2-selenopentyl)-1,3-ditellurane, 2,3-, 2,5-, 2,6- or 3,5-bis(3,4-epithio-1-selenobutyl)-1-thia-4-tellurane, 2,3-, 2,5-, 2,6- or 3,5-bis(4,5-epithio-2-selenopentyl)-1-thia-4-tellurane, 2,4- or 4,5-bis(3,4-epithio-1-selenobutyl)-1,3-ditellurolane, 2,4- or 4,5-bis(4,5-epithio-2-selenopentyl)-1,3-ditellurolane, 2,4-, 2,5- or 4,5-bis(3,4-epithio-1-selenobutyl)-1-thia-3-tellurolane, 2,4-, 2,5- or 4,5-bis(4,5-epithio-2-selenopentyl)-1-thia-3-tellurolane, 2,6-bis(4,5-epithio-2-selenopentyl-1,3,5-tritellurane, bis(3,4-epithio-1-selenobutyl)tricyclotelluraoctane, bis(3,4-epithio-1-selenobutyl)dicyclotelluranonane, 2,3-, 2,4-, 2,5- or 3,4-bis(3,4-epithio-1-selenobutyl)tellurophane, 2,3-, 2,4-, 2,5- or 3,4-bis(4,5-epithio-2-selenopentyl)tellurophane, 2-(4,5-thioepoxy-2-selenopentyl)-5-(3,4-thioepoxy-1-selenobutyl)-1-telluracyclohexane, 2,3-, 2,4-, 2,5-, 2,6-, 3,4-, 3,5- or 4,5-bis(3,4-thioepoxy-1-selenobutyl)-1-telluracyclohexane, 2,3-, 2,4-, 2,5-, 2,6-, 3,4-, 3,5- or 4,5-bis(4,5-thioepoxy-2-selenopentyl)-1-telluracyclohexane, 1,3- or 1,4-bis(β-epithiopropylseleno)benzene, 1,3- or 1,4-bis(β-epithiopropylselenomethyl)benzene, bis[4-(β-epithiopropylseleno)phenyl]methane, 2,2-bis[4-(β-epithiopropylseleno)phenyl]propane, bis[4-(β-epithiopropylseleno)phenyl]sulfide, bis[4-(β-epithiopropylseleno)phenyl]sulfone, and 4,4'-bis(β-epithiopropylseleno)biphenyl.

(6) Episulfide Compounds Having at Least One Epithioalkyltelluro Group

Bis(β-epithiopropyl) telluride, bis(β-epithiopropyl) ditelluride, bis(β-epithiopropyl)tri telluride, bis(β-epithiopropyltelluro)methane, 1,2-bis(β-epithiopropyltelluro)ethane, 1,3-bis(β-epithiopropyltelluro)propane, 1,2-bis(β-epithiopropyltelluro)propane, 1-(β-epithiopropyltelluro)-2-(β-epithiopropyltelluromethyl)propane, 1,4-bis(β-epithiopropyltelluro)butane, 1,3-bis(β-epithiopropyltelluro)butane, 1-(β-epithiopropyltelluro)-3-(β-epithiopropyltelluromethyl)butane, 1,5-bis(β-epithiopropyltelluro)pentane, 1-(β-epithiopropyltelluro)-4-(β-epithiopropyltelluromethyl)pentane, 1,6-bis(β-epithiopropyltelluro)hexane, 1-(β-epithiopropyltelluro)-5-(β-epithiopropyltelluroethyl)thio]ethane, 1-(β-epithiopropyltelluro)-2-[[2-(2-β-epithiopropyltelluroethyl)telluroethyl]thio]ethane, tetrakis(β-epithiopropyltelluromethyl)methane, 1,1,1-tris(β-epithiopropyltelluromethyl)propane, 1,5-bis(β-epithiopropyltelluro)-2-(β-epithiopropyltelluromethyl)-3-thiapentane, 1,5-bis(β-epithiopropyltelluro)-2,4-bis(β-epithiopropyltelluromethyl)-3-thiapentane, 1-(β-epithiopropyltelluro)-2,2-bis(β-epithiopropyltelluromethyl)-4-thiahexane, 1,5,6-tris(β-epithiopropyltelluromethyl)-4-(β-epithiopropyltelluromethyl)-3-thiahexane, 1,8-bis(β-epithiopropyltelluro)-4-(β-epithiopropyltelluromethyl)-3,6-dithiaoctane, 1,8-bis(β-epithiopropyltelluro)-4,5bis(β-epithiopropyltelluromethyl)-3,6-dithiaoctane, 1,8-bis(β-epithiopropyltelluro)-4,4-bis(β-epithiopropyltelluromethyl)-3,6-dithiaoctane, 1,8-bis(β-epithiopropyltelluro)-2,4,5-tris(β-epithiopropyltelluromethyl)-3,6-dithiaoctane, 1,8-bis(β-epithiopropyltelluro)-2,5-bis(β-epithiopropyltelluromethyl)-3,6-dithiaoctane, 1,9-bis(β-epithiopropyltelluro)-5-(β-epithiopropyltelluromethyl)-5-[(2-β-epithiopropyltelluroethyl)selenomethyl]-3,7-dithianonane, 1,10-bis(β-epithiopropyltelluro)-5,6-bis[(2-β-epithiopropyltelluroethyl)thio]-3,6,9-trithiadecane, 1,11-bis(β-epithiopropyltelluro)-4,8-bis(β-epithiopropyltelluromethyl)-3,6,9-trithiaundecane, 1,11-bis(β-epithiopropyltelluro)-5,7-bis(β-epithiopropyltelluromethyl)-3,6,9-trithiaundecane, 1,11-bis(β-epithiopropyltelluro)-5,7-[(2-β-epithiopropyltelluroethyl)selenomethyl]-3,6,9-trithiaundecane, 1,11-bis(β-epithiopropyltelluro)-4,7-bis(β-epithiopropyltelluromethyl)-3,6,9-trithiaundecane, tetra[2-(β-epithiopropyltelluro)acetylmethyl]methane, 1,1,1-tri[2-(β-epithiopropyltelluro)acetylmethyl]propane, tetra[2-(β-epithiopropyltelluromethyl)acetylmethyl]methane, 1,1,1-tri[2-(β-epithiopropyltelluromethyl)acetylmethyl]propane, bis(5,6-epithio-3-tellurohexyl) selenide, 2,3-bis(6,7-thioepoxy-1-selena-4-telluroheptyl)-1-(3,4-thioepoxy-1-tellurobutyl)propane, 1,1,3,3,-tetrakis(4,5-thioepoxy-2-telluropentyl)-2-selenapropane, bis(4,5-thioepoxy-2-telluropentyl)-3,6,9-triselenaundecane-1,11-bis(3,4-thioepoxy-1-tellurobutyl), 1,4-bis(3,4-thioepoxy-1-tellurobutyl)-2,3-bis(6,7-thioepoxy-1-selena-4-telluroheptyl)butane, tris(4,5-thioepoxy-2-telluropentyl)-3-selena-6-thiaoctane-1,8-bis(3,4-thioepoxy-1-tellurobutyl), bis(5,6-epithio-3-tellurohexyl) telluride, 2,3-bis(6,7-thioepoxy-1-tellura-4-telluroheptyl)-1-(3,4-thioepoxy-1-tellurobutyl)propane, 1,1,3,3,-tetrakis(4,5-thioepoxy-2-telluropentyl)-2-tellurapropane, bis(4,5-thioepoxy-2-telluropentyl)-3,6,9-tritelluraundecane-1,11-bis(3,4-thioepoxy-1-tellurobutyl), 1,4-bis(3,4-thioepoxy-1-tellurobutyl)-2,3-bis(6,7-thioepoxy-1-tellura-4-telluroheptyl)butane, tris(4,5-thioepoxy-2-telluropentyl)-3-tellura-6-thiaoctane-1,8-bis(3,4-thioepoxy-1-tellurobutyl), 1,3- or 1,4-bis(β-epithiopropyltelluro)cyclohexane, 1,3- or 1,4-bis(β-epithiopropyltelluromethyl)cyclohexane, bis[4-(β-epithiopropyltelluro)cyclohexyl]methane, 2,2-bis[4-(β-epithiopropyltelluro)cyclohexyl]propane, bis[4-(β-epithiopropyltelluro)cyclohexyl]sulfide, 2,5-bis(13-epithiopropyltelluromethyl)-1,4-dithiane, 2,5-bis(β-epithiopropyltelluroethylthiomethyl)-1,4-dithiane, 2,3-, 2,5- or 2,6-bis(3,4-epithio-1-tellurobutyl)-1,4-diselenane, 2,3-, 2,5- or 2,6-bis(4,5-epithio-2-telluropentyl)-1,4-diselenane, 2,4-, 2,5- or 5,6-bis(3,4-epithio-1-tellurobutyl)-1,3-diselenane, 2,4-, 2,5- or 5,6-bis(4,5-epithio-2-telluropentyl)-1,3-diselenane, 2,3-, 2,5-, 2,6- or 3,5-bis(3,4-epithio-1-tellurobutyl)-1-thia-4-selenane, 2,3-, 2,5-, 2,6- or 3,5-bis(4,5-epithio-2-telluropentyl)-1-thia-4-selenane, 2,4- or 4,5-bis(3,4-epithio-1-tellurobutyl)-1,3-diselenolane, 2,4- or 4,5-bis(4,5-epithio-2-telluropentyl)-1,3-diselenolane, 2,4-, 2,5- or 4,5-bis(3,4-epithio-1-tellurobutyl)-1-thia-3-selenolane, 2,4-, 2,5- or 4,5-bis(4,5-epithio-2-telluropentyl)-1-thia-3-selenolane, 2,6-bis(4,5-epithio-2-telluropentyl-1,3,5-triselenane, bis(3,4-epithio-1-tellurobutyl)tricycloselenaoctane, bis(3,4-epithio-1-tellurobutyl)dicycloselenanonane, 2,3-, 2,4-, 2,5- or 3,4-bis(3,4-epithio-1-tellurobutyl)selenophane, 2,3-, 2,4-, 2,5- or 3,4-bis(4,5-epithio-2-telluropentyl)selenophane, 2-(4,5-thioepoxy-2-telluropentyl)-5-(3,4-thioepoxy-1-tellurobutyl)-1-selenacyclohexane, 2,3-, 2,4-, 2,5-, 2,6-, 3,4-, 3,5- or 4,5-bis(3,4-thioepoxy-1-tellurobutyl)-1-selenacyclohexane, 2,3-, 2,4-, 2,5-, 2,6-, 3,4-, 3,5- or 4,5-bis(4,5-thioepoxy-2-telluropentyl)-1-selenacyclohexane, 2,3-, 2,5- or 2,6-bis(3,4-epithio-1-tellurobutyl)-1,4-ditellurane, 2,3-, 2,5- or 2,6-bis(4,5-epithio-2-telluropentyl)-1,4-ditellurane, 2,4-, 2,5- or 5,6-bis(3,4-epithio-1-tellurobutyl)-1,3-ditellurane, 2,4-, 2,5- or 5,6-bis(4,5-epithio-2-telluropentyl)-1,3-ditellurane, 2,3-, 2,5-, 2,6- or 3,5-bis(3,4-epithio-1-tellurobutyl)-1-thia-4-tellurane, 2,3-, 2,5-, 2,6- or 3,5-bis(4,5-epithio-2-telluropentyl)-1-thia-4-tellurane, 2,4- or 4,5-bis(3,4-epithio-1-tellurobutyl)-1,3-ditellurolane, 2,4- or 4,5-bis(4,5-epithio-2-telluropentyl)-1,3-ditellurolane, 2,4-, 2,5- or 4,5-bis(3,4-epithio-1-tellurobutyl)-1-thia-3-tellurolane, 2,4-, 2,5- or 4,5-bis(4,5-epithio-2-telluropentyl)-1-thia-3-tellurolane, 2,6-bis(4,5-epithio-2-telluropentyl-1,3,5-tritellurane, bis(3,4-epithio-1-tellurobutyl)tricyclotelluraoctane, bis(3,4-epithio-1-tellurobutyl)dicyclotelluranonane, 2,3-, 2,4-, 2,5- or 3,4-bis(3,4-epithio-1-tellurobutyl)tellurophane, 2,3-, 2,4-, 2,5- or 3,4-bis(4,5-epithio-2-telluropentyl)tellurophane, 2-(4,5-thioepoxy-2-telluropentyl)-5-(3,4-thioepoxy-1-tellurobutyl)-1-telluracyclohexane, 2,3-, 2,4-, 2,5-, 2,6-, 3,4-, 3,5- or 4,5-bis(3,4-thioepoxy-1-tellurobutyl)-1-telluracyclohexane, 2,3-, 2,4-, 2,5-, 2,6-, 3,4-, 3,5- or 4,5-bis(4,5-thioepoxy-2-telluropentyl)-1-telluracyclohexane, 1,3- or 1,4-bis(β-epithiopropyltelluro)benzene, 1,3- or 1,4-bis(β-epithiopropyltelluromethyl)benzene, bis[4-(β-epithiopropyltelluro)phenyl]methane, 2,2-bis[4-(β-epithiopropyltelluro)phenyl]propane, bis[4-(β-epithiopropyltelluro)phenyl]sulfide, bis[4-(β-epithiopropyltelluro)phenyl]sulfone, and 4,4'-bis(β-epithiopropyltelluro)biphenyl.

(7) Episulfide Compounds Having Unsaturated Group

Vinylphenyl thioglycidyl ether, vinylbenzyl thioglycidyl ether, thioglycidyl methacrylate, thioglycidyl acrylate, and allyl thioglycidyl ether.

(8) Other Episulfide Compounds

Ethylene sulfide, propylene sulfide, thioglycidol, thioglycidyl acetate, thioglycidyl propionate, and thioglycidyl benzoate.

The episulfide compounds referred to herein may further include the compounds derived from the above episulfide compounds by replacing at least one hydrogen of its epithio group with methyl group.

The episulfide compounds having an epi(di)thioethyl group represented by the formula 2 may be used alone or in combination of two or more, and preferably used in an amount of 1 to 95 arts by weight based on 100 parts by weight of the alicyclic compound.

To improve the properties such as oxidation resistance, weathering resistance, dyeability, strength and refractive index, the composition for optical materials of the present invention may further contain an compound capable of reacting with the alicyclic compound and/or the additive compound (episulfide compound) in an amount of 1 to 50 parts by weight based on 100 parts by weight of the alicyclic compound. Such a compound is hereinafter referred to as "additive compound." A composition containing the additive compound is cured by polymerization, if necessary, in the presence of a known catalyst for curing by polymerization.

The additive compound may include epoxy compounds, iso(thio)cyanates, carboxylic acids, carboxylic anhydrides, phenol compounds, amines, vinyl compounds, allyl compounds, acryl compounds, methacryl compounds, mercaptans, inorganic compounds having sulfur atom, and inorganic compounds having selenium atom. Examples thereof are shown below.

(1) Epoxy Compounds (i) Monoepoxy compounds such as ethylene oxide and propylene oxide;

(ii) Phenolic epoxy compounds produced by condensing epihalohydrins with polyhydric phenol compounds such as hydroquinone, catechol, resorcinol, bisphenol A, bisphenol F, bisphenol ether, halogenated bisphenol A and novolak resins;

(iii) Alcoholic epoxy compounds produced by condensing epihalohydrins with alcohol compounds such as methanol, ethanol, propanol, butanol, ethylene glycol; diethylene glycol triethylene glycol, polyethylene glycol, propylene glycol, dipropylene glycol, polypropylene glycol, 1,3-propanediol, 1,4-butanediol, 1,6-hexanediol, neopentyl glycol, glycerol, trimethylolpropane, pentaerythritol, 1,3- or 1,4-cyclohexanediol, 1,3- or 1,4-cyclohexanedimethanol, hydrogenated bisphenol A, bisphenol A-ethylene oxide adducts, and bisphenol A-propylene oxide adducts;

(iv) Urethane epoxy compounds produced by the reaction of diisocyanate compounds with the above alcohol compounds or phenol compounds;

(v) Glycidyl ester epoxy compounds produced by condensing epihalohydrins with carboxylic acids such as acetic acid, propionic acid, benzoic acid, adipic acid, sebacic acid, dodecandicarboxylic acid, dimer acid, phthalic acid, isophthalic acid, terephthalic acid, tetrahydrophthalic acid, methyltetrahydrophthalic acid, hexahydrophthalic acid, HET acid, nadic acid, maleic acid, succinic acid, fumaric acid, trimellitic acid, benzenetetracarboxylic acid, benzophenonetetracarboxylic acid, naphthalenedicarboxylic acid and diphenyldicarboxylic acid, acrylic acid, methacrylic acid, and fumaric acid;

(vi) Amine epoxy compounds produced by condensing epihalohydrins with amine compounds such as ethylenediamine, 1,2-diaminopropane, 1,3-diaminopropane, 1,2-diaminobutane, 1,3-diaminobutane, 1,4-diaminobutane, 1,5-diaminopentane, 1,6-diaminohexane, 1,7-diaminoheptane, 1,8-diaminooctane, bis(3-aminopropyl)ether, 1,2-bis(3-aminopropoxy)ethane, 1,3-bis(3-aminopropoxy)-2,2'-dimethylpropane, 1,2-, 1,3- or 1,4-bisaminocyclohexane, 1,3- or 1,4-bisaminomethylcyclohexane, 1,3- or 1,4-bisaminoethylcyclohexane, 1,3- or 1,4-bisaminopropylcyclohexane, hydrogenated 4,4'-diaminodiphenylmethane, isophoronediamine, 1,4-bisaminopropylpiperadine, m- or β-phenylenediamine, 2,4- or 2,6-tolylenediamine, m- or p-xylylenediamine, 1,5- or 2,6-naphthalenediamine, 4,4'-diaminodiphenylmethane, 4,4'-diaminodiphenyl ether, 2,2-(4,4'-diaminodiphenyl)propane, N,N'-dimethylethylenediamine, N,N'-dimethyl-1,2-diaminopropane, N,N'-dimethyl-1,3-diaminopropane, N,N'-dimethyl-1,2-diaminobutane, N,N'-dimethyl-1,3-diaminobutane, N,N'-dimethyl-1,4-diaminobutane, N,N'-dimethyl-1,5-diaminopentane, N,N'-dimethyl-1,6-diaminohexane, N,N'-dimethyl-1,7-diaminoheptane, N,N'-diethylethylenediamine, N,N'-diethyl-1,2-diaminopropane, N,N'-diethyl-1,3-diaminopropane, N,N'-diethyl-1,2-diaminobutane, N,N'-diethyl-1,3-diaminobutane, N,N'-diethyl-1,4-diaminobutane, N,N'-diethyl-1,6-diaminohexane, piperadine, 2-methylpiperadine, 2,5- or 2,6-dimethylpiperadine, homopiperadine, 1,1-di(4-piperidyl)methane, 1,2-di(4-piperidyl)ethane, 1,3-di(4-piperidyl)propane, and 1,4-di(4-piperidyl)butane;

(vii) Sulfur-containing epoxy compounds such as bis(β-epoxypropyl) sulfide, bis(β-epoxypropylthio)methane, 1,2-bis(β-epoxypropylthio)ethane, 1,3-bis(β-epoxypropylthio)propane, 1,2-bis(β-epoxypropylthio)propane, 1-(β-epoxypropylthio)-2-(β-epoxypropylthiomethyl)propane, 1,4-bis(β-epoxypropylthio)butane, 1,3-bis(β-epoxypropylthio)butane, 1-(β-epoxypropylthio)-3-(β-epoxypropylthiomethyl)butane, 1,5-bis(β-epoxypropylthio)pentane, 1-(β-epoxypropylthio)-4-(β-epoxypropylthiomethyl)pentane, 1,6-bis(β-epoxypropylthio)hexane, 1-(β-epoxypropylthio)-5-(β-epoxypropylthiomethyl)hexane, 1-(β-epoxypropylthio)-2-[(2-β-epoxypropylthioethyl)thio]ethane, 1-(β-epoxypropylthio)-2-[[2-(2-β-epoxypropylthioethyl)thioethyl]thio]ethane, tetrakis(β-epoxypropyl-thiomethyl)methane, 1,1,1-tris(β-epoxypropylthiomethyl)propane, 1,5-bis(β-epoxypropylthio)-2-(β-epoxypropylthiomethyl)-3-thiapentane, 1,5-bis(β-epoxypropylthio)-2,4-bis(β-epoxypropylthiomethyl)-3-thiapentane, 1-(β-epoxypropylthio)-2,2-bis(β-epoxypropylthiomethyl)-4-thiahexane, 1,5,6-tris(β-epoxypropylthio)-4-(β-epoxypropylthiomethyl)-3-thiahexane, 1,8-bis(β-epoxypropylthio)-4-(β-epoxypropylthiomethyl)-3,6-dithiaoctane, 1,8-bis(β-epoxypropylthio)-4,5-bis(β-epoxypropylthiomethyl)-3,6-dithiaoctane, 1,8-bis(β-epoxypropylthio)-4,4-bis(β-epoxypropylthiomethyl)-3,6-dithiaoctane, 1,8-bis(β-epoxypropylthio)-2,4,5-tris(β-epoxypropylthiomethyl)-3,6-dithiaoctane, 1,8-bis(β-epoxypropylthio)-2,5-bis(β-epoxypropylthiomethyl)-3,6-dithiaoctane, 1,9-bis(β-epoxypropylthio)-5-(β-epoxypropylthiomethyl)-5-[(2-β-epoxypropylthioethyl)thiomethyl]-3,7-dithianonane, 1,10-bis(β-epoxypropylthio)-5,6-bis[(2-β-epoxypropylthioethyl)thio]-3,6,9-trithiadecane, 1,11-bis(β-epoxypropylthio)-4,8-bis(β-epoxypropylthiomethyl)-3,6,9-trithiaundecane, 1,11-bis(β-epoxypropylthio)-5,7-bis(β-epoxypropylthiomethyl)-3,6,9-trithiaundecane, 1,11-bis(β-epoxypropylthio)-5,7-[(2-β-epoxypropylthioethyl)thiomethyl]-3,6,9-trithiaundecane, 1,11-bis(β-epoxypropylthio)-4,7-bis(β-epoxypropylthiomethyl)-3,6,9-trithiaundecane, 1,3- or 1,4-bis(β-epoxypropylthio)cyclohexane, 1,3- or 1,4-bis(β-epoxypropylthiomethyl)cyclohexane, bis[4-(β-epoxypropylthio)cyclohexyl]methane, 2,2-bis[4-(β-epoxypropylthio)cyclohexyl]propane, bis[4-(β-epoxypropylthio)cyclohexyl]sulfide, 2,5-bis(β-epoxypropylthiomethyl)-1,4-dithiane, 1,3- or 1,4-bis(β-epoxypropylthio)benzene, 1,3- or 1,4-bis(β-epoxypropylthiomethyl)benzene, bis[4-(β-epoxypropylthio)phenyl]methane, 2,2-bis[4-(β-epoxypropylthio)phenyl]propane, bis[4-(β-epoxypropylthio)phenyl]sulfide, bis[4-(β-epoxypropylthio)phenyl]sulfone, and 4,4'-bis(β-epoxypropylthio)biphenyl;

(viii) Alicyclic epoxy compounds such as 3,4-epoxycyclohexyl-3,4-epoxycyclohexanecarboxylate, vinylcyclohexane dioxide, 2-(3,4-epoxycyclohexyl)-5,5-spiro-3,4-epoxycyclohexane-meta-dioxane, and bis(3,4-epoxycyclohexyl)adipate;

(ix) Epoxidized compounds of unsaturated compounds, such as cyclopentadiene epoxide, epoxidized soy bean oil, epoxidized polybutadiene, and vinylcyclohexene epoxide; and (x) Epoxy compounds having unsaturated group such as vinylphenyl glycidyl ether, vinylbenzyl glycidyl ether, glycidyl methacrylate, glycidyl acrylate, and allyl glycidyl ether.

(2) Iso(thio)cyanates (i) Monoisocyanates such as methyl isocyanate, ethyl isocyanate, propyl isocyanate, isopropyl isocyanate, n-butyl isocyanate, sec-butyl isocyanate, tert-butyl isocyanate, pentyl isocyanate, hexyl isocyanate, octyl isocyanate, dodecyl isocyanate, cyclohexyl isocyanate, phenyl isocyanate, and tolyl isocyanate;

(ii) Polyisocyanates such as diethylene diisocyanate, tetramethylene diisocyanate, hexamethylene diisocyanate, trimethylhexamethylene diisocyanate, cyclohexane diisocyanate, 1,3-bis(isocyanatomethyl)cyclohexane, 1,4-bis(isocyanatomethyl)cyclohexane, isophorone diisocyanate, 2,6-bis(isocyanatomethyl)decahydronaphthalene, lysine triisocyanate, 2,4-tolylenediisocyanate, 2,6-tolylene diisocyanate, o-tolydyne diisocyanate, 4,4'-diphneylmethane diisocyanate, diphenyl ether diisocyanate, 3-(2'-isocyanatocyclohexyl)propyl isocyanate, tris(phenylisocyanate)thiophosphate, isopropylidene bis(cyclohexylisocyanate), 2,2'-bis(4-isocyanatophenyl)propane, triphenylmethane triisocyanate, bis(diisocyanatotolyl)phenylmethane, 4,4',4"-triisocyanato-2,5-dimethoxyphenylamine, 3,3'-dimethoxybenzidine-4,4'-diisocyanate, 1,3-phenylene diisocyanate, 1,4-phenylene diisocyanate, 4,4'-diisocyanatobiphenyl, 4,4'-diisocyanato-3,3'-dimethylbiphenyl, dicyclohexylmethan-4,4'-diisocyanate, 1,1'-methylenebis(4-isocyanatobenzene), 1,1'-methylenebis(3-methyl-4-isocyanatobenzene), m-xylylene diisocyanate, p-xylylene diisocyanate, 1,3-bis(1-isocyanato-1-methylethyl)benzene, 1,4-bis(1-isocyanato-1-methylethyl)benzene, 1,3-bis(2-isocyanato-2-propyl)benzene, 2,6-bis(isocyanatomethyl)naphthalene, 1,5-naphthalene diisocyanate, bis(isocyanatomethyl)tetrahydrodicyclopentadiene, bis(isocyanatomethyl)dicyclopentadiene, bis(isocyanatomethyl)tetrahydrothiophene, 2,5-bis(isocyanatomethyl)norbornene, bis(isocyanatomethyl)adamantane, thiodiethyl diisocyanate, thiodipropyl diisocyanate, thiodihexyl diisocyanate, bis[(4-isocyanatomethyl)phenyl]sulfide, 2,5-diisocyanato-1,4-dithiane, 2,5-diisocyanatomethyl-1,4-dithiane, 2,5-diisocyanatomethyl thiophene, dithiodiethyl diisocyanate, dithiodipropyl diisocyanate, dimeric acid diisocyanate, and 1,3,5-tri(1-isocyanatohexyl)isocyanuric acid;

(iii) Isocyanates such as dimers produced by biuret reaction of the preceding polyisocyanates, cyclic trimers of the preceding polyisocyanates, and adducts of the preceding polyisocyanates with alcohols or thiols; and (iv) Isothiocyanates corresponding to the preceding isocyanates having its isocyanate group or groups replaced by isothiocyanate group or groups partly or completely.

(3) Carboxylic Acids

Acetic acid, propionic acid, benzoic acid, adipic acid, sebacic acid, dodecandicarboxylic acid, dimer acid, phthalic acid, isophthalic acid, terephthalic acid, tetrahydrophthalic acid, methyltetrahydrophthalic acid, hexahydrophthalic acid, HET acid, nadic acid, maleic acid, succinic acid, fumaric acid, trimellitic acid, benzenetetracarboxylic acid, benzophenonetetracarboxylic acid, naphthalenedicarboxylic acid and diphenyldicarboxylic acid, acrylic acid, methacrylic acid, and fumaric acid.

(4) Carboxylic Anhydrides

Anhydrides of carboxylic acids described above.

(5) Phenol Compounds

Polyhydric phenol compounds such as hydroquinone, catechol, resorcinol, bisphenol A, bisphenol F, bisphenol ether, halogenated bisphenol A and novolak resins.

(6) Amines

Amines described in "(1) Epoxy compounds."

(7) Vinyl Compounds

Vinyl ether, ethyl vinyl ether, isobutyl vinyl ether, 2-ethylhexyl vinyl ether, phenyl vinyl ether, benzyl vinyl ether, 2-chloroethyl vinyl ether, cyclohexyl vinyl ether, vinyl glycidyl ether, vinylalcohol, methylvinylcarbinol, ethylene glycol monovinyl ether, ethylene glycol divinyl ether, diethylene glycol monovinyl ether, diethylene glycol divinyl ether, tetramethylene glycol monovinyl ether, divinyl sulfide, vinyl ethyl sulfide, vinyl phenyl sulfide, methyl vinyl ketone, divinyl dicarbonate, vinyl diglycol carbonate, vinylene carbonate, vinyl acetate, vinyl chloroacetate, vinyl propionate, vinyl butylate, vinyl hexanoate, vinyl 2-ethylhexanoate, divinyl adipate, vinyl benzoate, vinyl salicylate, vinyl acrylate, vinyl methacrylate, vinyl bromide, vinyl iodide, vinylphosphoric acid, vinylurea, styrene, 2-methylstyrene, 3-methylstyrene, 4-methylstyrene, α-methylstyrene, 2,4,6-trimethylstyrene, 4-t-butylstyrene, stilbene, vinylphenol, 3-vinylbenzyl alcohol, 4-vinylbenzyl alcohol, 2-(4-vinylphenylthio)ethanol, 2-(3-vinylphenylthio)ethanol, 2-(4-vinylbenzylthio)ethanol, 2-(3-vinylbenzylthio)ethanol, 1,3-bis(4-vinylbenzylthio)-2-propanol, 1,3-bis(3-vinylbenzylthio)-2-propanol, 2,3-bis(4-vinylbenzylthio)-1-propanol, 2,3-bis(3-vinylbenzylthio)-1-propanol, cinnamyl alcohol, cinnamaldehyde, 1,3-divinylbenzene, 1,4-divinylbenzene, trivinylbenzene, divinyl phthalate, 2-chlorostyrene, 3-chlorostyrene, 4-chlorostyrene, 3-chloromethylstyrene, 4-chloromethylstyrene, 4-aminostyrene, 3-cyanomethylstyrene, 4-cyanomethylstyrene, 4-vinylbiphenyl, 2,2'-divinylbiphenyl, 4,4'-divinylbiphenyl, 2,2'-distyryl ether, 4,4'-distyryl ether, 2,2'-distyryl sulfide, 4,4'-distyryl sulfide, 2,2-bis(4-vinylphenyl)propane, bis(4-vinylphenyl)ether, and 2,2-bis(4-vinyloxyphenyl)propane.

(8) Allyl Compounds

Compounds described in "(7) Vinyl compounds" having its vinyl group replaced by ally group partially or completely.

(9) Acryl Compounds

Methyl acrylate, ethyl acrylate, propyl acrylate, butyl acrylate, cyclohexyl acrylate, 2-hydroxyethyl acrylate, 3-hydroxypropyl acrylate, 2-hydroxypropyl acrylate, 3-phenoxy-2-hydroxypropyl acrylate, trimethylolpropane monoacrylate, 2-hydroxyethyl isocyanurate monoacrylate, 2-hydroxyethyl isocyanurate diacrylate, 2-hydroxyethyl cyanurate monoacrylate, 2-hydroxyethyl cyanurate diacrylate, ethylene glycol diacrylate, diethylene glycol diacrylate, 1,3-butylene glycol diacrylate, triethylene glycol diacrylate, polyethylene glycol diacrylate, propylene glycol diacrylate, 1,3-propanediol diacrylate, 1,3-butanediol diacrylate, 1,4-butanediol diacrylate, 1,6-hexanediol diacrylate, neopentyl glycol diacrylate, polypropylene glycol diacrylate, 2-hydroxy-1,3-diacryloxypropane, 2,2-bis[4-(acryloxyethoxy)phenyl]propane, 2,2-bis[4-(acryloxyethoxy)cyclohexyl]propane, 2,2-bis[4-(2-hydroxy-3-acryloxypropoxy)phenyl]propane, 2,2-bis[4-(acryloxy.diethoxy)phenyl]propane, 2,2-bis[4-(acryloxy.polyethoxy)phenyl]propane, trimethylolpropane triacrylate, pentarythritol monoacrylate, pentarythritol diacrylate, pentarythritol triacrylate, pentarythritol tetraacrylate, bis(2,2,2-trimethylolethyl)ether pentaacrylate, bis(2,2,2-trimethylolethyl)ether hexaacrylate, and bis(4-acryloylthiophenyl)sulfide.

(10) Methacryl Compounds

Compounds described in "(9) Acryl compounds" having its acryl group replaced by methacryl group partially or completely.

(11) Mercaptans

Aliphatic mercaptans such as methyl mercaptan, ethyl mercaptan, n-propyl mercaptan, n-butyl mercaptan, allyl mercaptan, n-hexyl mercaptan, n-octyl mercaptan, n-decyl mercaptan, n-dodecyl mercaptan, n-tetradecyl mercaptan, n-hexadecyl mercaptan, n-octadecyl mercaptan, cyclohexyl mercaptan, isopropyl mercaptan, tert-butyl mercaptan, tert-nonyl mercaptan, tert-dodecyl mercaptan, phenyl mercaptan, benzyl mercaptan, 3-methylphenyl mercaptan, 4-methylphenyl mercaptan, 4-chlorobenzyl mercaptan, 4-vinylbenzyl mercaptan, 3-vinylbenzyl mercaptan, methyl mercaptopropionate, 2-mercaptoethanol, 3-mercapto-1,2-propanediol, 2-mercapto-1,3-propanediol, mercaptoacetic acid, mercaptoglycolic acid, mercaptopropionic acid, methanedithiol, 1,2-dimercaptoethane, 1,2-dimercaptopropane, 1,3-dimercaptopropane, 2,2-dimercaptopropane, 1,4-dimercaptobutane, 1,6-dimercaptohexane, bis(2-mercaptoethyl)ether, bis(2-mercaptoethyl)sulfide, 1,2-bis(2-mercaptoethyloxy)ethane, 1,2-bis(2-mercaptoethylthio)ethane, 2,3-dimecrapto-1-propanol, 1,3-dimercapto-2-propanol, 1,2,3-trimercaptopropane, 2-mercaptomethyl-1,3-dimercaptopropane, 2-mercaptomethyl-1,4-dimercaptobutane, 2-(2-mercaptoethylthio)-1,3-dimercaptopropane, 4-mercaptomethyl-1,8-dimercapto-3,6-dithiaoctane, 2, A4-dimercaptomethyl-1,5-dimercapto-3-thiapentane, 4,8-dimercaptomethyl-1,11-dimercapto-3,6,9-trithiaundecane, 4,7-dimercaptomethyl-1,11-dimercapto-3,6,9-trithiaundecane, 5,7-dimercaptomethyl-1,11-dimercapto-3,6,9-trithiaundecane, 1,1,1-tris(mercaptomethyl)propane, tetrakis(mercaptomethyl)methane, ethylene glycol bis(2-mercaptoacetate), ethylene glycol bis(3-mercaptopropionate), diethylene glycol bis(2-mercaptoacetate), diethylene glycol bis(3-mercaptopropionate), 1,4-butanediol bis(2-mercaptoacetate), 1,4-butanediol bis(3-mercaptopropionate), trimethylolpropane tris(2-mercaptoacetate), trimethylolpropane tris(3-mercaptopropionate), pentaerythritol tetrakis(2-mercaptoacetate), pentaerythritol tetrakis(3-mercaptopropionate), 1,2-dimercaptocyclohexane, 1,3-dimercaptocyclohexane, 1,4-dimercaptocyclohexane, 1,3-bis-(mercaptomethyl)cyclohexane, 1,4-bis(mercaptomethyl)cyclohexane, 2,5-bis(mercaptomethyl)-1,4-dithiane, 2,5-bis(2-mercaptoethyl)-1,4-dithiane, 2,5-bis(2-mercaptoethylthiomethyl)-1,4-dithiane, 2,5-bis(mercaptomethyl)-1-thiane, 2,5-bis(2-mercaptoethyl)-1-thiane, 2,5-bis(mercaptomethyl)thiophene, 1,2-epithiomercaptoethane, 1,2-epithio-1,2-demercaptoethane, 1,2-epithio-1,2,3,4-tetramercaptoethane, 1,2-epithio-3-mercaptopropane, 1,2-epithio-3,3-demercaptopropane, 1,2-epithio-3,3,3-trimercaptopropane, 2,3-epithio-1,4-demercaptotutane, 2,3-epithio-1,1,4,4-tetramercaptobutane, 1,2-epithio-5-mercapto-4-thiapentane, 1,2-epithio-5,5-demercapto-4-thiapentane, 1,2-epithio-5,5,5-trimercapto-4-thiapentane, 1,2:6,7-deepithio-1,7-demercapto-5-thiaheptane, and 1,2:6,7-deepithio-3,5-demercapto-5-thiaheptane; and aromatic mercaptans such as 1,2-Dimercaptobenzene, 1,3-dimercaptobenzene, 1,4-dimercaptobenzene, 1,3-bis(mercaptomethyl)benzene, 1,4-bis(mercaptomethyl)benzene, 2,2'-dimercaptobiphenyl, 4,4'-dimercaptobiphenyl, bis(4-mercaptophenyl)methane, 2,2-bis(4-mercaptophenyl)propane, bis(4-mercaptophenyl)ether, bis(4-mercaptophenyl) sulfide, bis(4-mercaptophenyl)sulfone, bis(4-mercaptomethylphenyl)methane, 2,2-bis(4-mercaptomethylphenyl)propane, bis(4-mercaptomethylphenyl)ether, bis(4-mercaptomethylphenyl)sulfide, 4-hydroxythiophenol, and mercaptobenzoic acid.

(12) Inorganic Compounds Having Sulfur Atom

Sulfur, hydrogen sulfide, carbon disulfide, carbon selenosulfide, ammonium sulfide, oxides of sulfur such as sulfur dioxide and sulfur trioxide, salts of thiocarbonic acid, sulfuric acid, salts of sulfuric acid, salts of hydrogensulfuric acid, salts of sulfurous acid, salts of hyposulfurous acid, salts of persulfuric acid, salts of thiocyanic acid, salts of thiosulfuric acid, halides such as sulfur dichloride, thionyl chloride and thiophosgen, boron sulfide, nitrogen sulfide, silicon sulfide, phosphorus sulfide, arsenic sulfide, metal sulfides, and metal hydrogensulfides.

(13) Inorganic Compounds Having Selenium Atom

Selenium, hydrogen selenide, selenium dioxide, carbon diselenide, ammonium selenide, oxides of selenium such as selenium dioxide, selenic acid, salts of selenic acid, selenous acid, salts of selenous acid, salts of hydrogenselenic acid, selenosulfuric acid, salts of selenosulfuric acid, selenopyrosulfuric acid, salts of selenopyrosulfuric acid, halides such as selenium tetrabromide and selenium oxychloride, salts of selenocyanic acid, boron selenide, phosphorus selenide, arsenic selenide, and metal selenides.

The composition for optical materials my be cured by polymerization, if necessary, in the presence of a curing catalyst such as amines, phosphines, quaternary ammonium salts, quaternary phosphonium salts, tertiary sulfonium salts, secondary iodonium salts, mineral acids, Lewis acids, organic acids, silicic acid compounds, tetrafluoroboric acid compounds, peroxides, azo compounds, condensates of aldehyde and ammonia compound, guanidine compounds, thiourea compounds, thiazole compounds, sulfenamide compounds, thiuram compounds, salts of dithiocarbamic acid, salts of xanthogenic acid, and esters of acid phosphoric acid. Examples of the curing catalysts are mentioned below.

(1) Amines

Primary amines such as ethylamine, n-propylamine, sec-propylamine, n-butylamine, sec-butylamine, isobutylamine, tert-butylamine, pentylamine, hexylamine, heptylamine, octylamine, decylamine, laurylamine, myristylamine, 1,2-dimethylhexylamine, 3-pentylamine, 2-ethylhexylamine, allylamine, aminoethanol, 1-aminopropanol, 2-aminopropanol, aminobutanol, aminopentanol, aminohexanol, 3-ethoxypropylamine, 3-propoxypropylamine, 3-isopropoxypropylamine, 3-butoxypropylamine, 3-isobutoxypropylamine, 3-(2-ethylhexyloxy)propylamine, aminocyclopentane, aminocyclohexane, aminonorbornene, aminomethylcyclohexane, aminobenzene, benzylamine, phenetylamine, α-phenylethylamine, naphthylamine and furfurylamine;

primary polyamines such as ethylenediamine, 1,2-diaminopropane, 1,3-diaminopropane, 1,2-diaminobutane, 1,3-diaminobutane, 1,4-diaminobutane, 1,5-diaminopentane, 1,6-diaminohexane, 1,7-diaminoheptane, 1,8-diaminooctane, dimethylaminopropylamine, diethylaminopropylamine, bis-(3-aminopropyl)ether, 1,2-bis-(3-aminopropoxy)ethane, 1,3-bis-(3-aminopropoxy)-2,2'-dimethylpropane, aminoethylethanolamine, 1,2-, 1,3- or 1,4-bisaminocyclohexane, 1,3- or 1,4-bisaminomethylcyclohexane, 1,3- or 1,4-bisaminoethylcyclohexane, 1,3- or 1,4-bisaminopropylcyclohexane, hydrogenated 4,4'-diaminodiphenylmethane, 2- or 4-aminopiperidine, 2- or 4-aminomethylpiperidine, 2- or 4-aminoethylpiperidine, N-aminoethylpiperidine, N-aminopropylpiperidine, N-aminoethylmorpholine, N-aminopropylmorpholine, isophoronediamine, menthanediamine, 1,4-bisaminopropylpiperadine, o-, m- or p-phenylenediamine, 2,4- or 2,6-tolylenediamine, 2,4-toluenediamine, m-aminobenzylamine, 4-chloro-o-phenylenediamine, tetrachloro-p-xylylenediamine, 4-methoxy-6-methyl-m-phenylenediamine, m- or p-xylylenediamine, 1,5- or 2,6-naphthalenediamine, benzidine, 4,4'-bis(o-toluidine), dianisidine, 4,4'-diaminodiphenylmethane, 2,2-(4,4'-diaminodiphenyl)propane, 4,4'-diaminodiphenyl ether, 4,4'-thiodianiline, 4,4'-diaminodiphenyl sulfone, 4,4'-diaminoditolyl sulfone, methylenebis(o-chloroaniline), 3,9-bis(3-aminopropyl)-2,4,8,10-tetraoxaspiro[5.5]undecane, diethylenetriamine, iminobispropylamine, methyliminobispropylamine, bis(hexamethylene)triamine, triethylenetetramine, tetraethylenepentamine, pentaethylenehexamine, N-aminoethylpiperadine, N-aminopropylpiperadine, 1,4-bis(aminoethylpiperadine), 1,4-bis(aminopropylpiperadine), 2,6-diaminopyridine, and bis(3,4-diaminophenyl)sulfone;

secondary amines such as diethylamine, dipropylamine, di-n-butylamine, di-sec-butylamine, diisobutylamine, di-n-pentylamine, di-3-pentylamine, dihexylamine, dioctylamine, di(2-ethylhexyl)amine, methylhexylamine, diallylamine, pyrrolidine, piperidine, 2-, 3- or 4-picoline, 2,4-, 2,6- or 3,5-lupetidine, diphenylamine, N-methylaniline, N-ethylaniline, dibenzylamine, methylbenzylamine, dinaphthylamine, pyrrol, indoline, indole, and morpholine;

secondary polyamines such as N,N'-dimethylethylenediamine, N,N'-dimethyl-1,2-diaminopropane, N,N'-dimethyl-1,3-diaminopropane, N,N'-dimethyl-1,2-diaminobutane, N,N'-dimethyl-1,3-diaminobutane, N,N'-dimethyl-1,4-diaminobutane, N,N'-dimethyl-1,5-diaminopentane, N,N'-dimethyl-1,6-diaminohexane, N,N'-dimethyl-1,7-diaminoheptane, N,N'-diethylethylenediamine, N,N'-diethyl-1,2-diaminopropane, N,N'-diethyl-1,3-diaminopropane, N,N'-diethyl-1,2-diaminobutane, N,N'-diethyl-1,3-diaminobutane, N,N'-diethyl-1,4-diaminobutane, N,N'-diethyl-1,6-diaminohexane, piperadine, 2-methylpiperadine, 2,5- or 2,6-dimethylpiperadine, homopiperadine, 1,1-di(4-piperidyl)methane, 1,2-di(4-piperidyl)ethane, 1,3-di(4-piperidyl)propane, 1,4-di(4-piperidyl)butane, and tetramethylguanidine;

tertiary amines such as trimethylamine, triethylamine, tri-n-propylamine, triisopropylamine, tri(1,2-dimethylpropyl)amine, tri(3-methoxypropyl)amine, tri-n-butylamine, triisobutylamine, tri-sec-butylamine, tri-n-pentylamine, tri-3-pentylamine, tri-n-hexylamine, tri-n-octylamine, tri(2-ethylhexyl)amine, tridodecylamine, trilaurylamine, dicyclohexylethylamine, cyclohexyldiethylamine, tricyclohexylamine, N. N-dimethylhexylamine, N-methyldihexylamine, N,N-dimethylcyclohexylamine, N-methyldicyclohexylamine, N,N-diethylethanolamine, N,N-dimethylethanolamine, N-ethyldiethanolamine, triethanolamine, tribenzylamine, N,N-dimethylbenzylamine, diethylbenzylamine, triphenylamine, N,N-dimethylamino-p-cresol, N,N-dimethylaminomethylphenol, 2-(N,N-dimethylaminomethyl)phenol, N,N-dimethylaniline, N,N-diethylaniline, pyridine, quinoline, N-methylmorpholine, N-methylpiperidine, and 2-(2-dimethylaminoethoxy)-4-methyl-1,3,2-dioxabornane;

tertiary polyamines such as tetramethylethylenediamine, pyrazine, N,N'-dimethylpiperadine, N,N'-bis(2-hydroxypropyl)piperadine, hexamethylenetetramine, N,N,N',N'-tetramethyl-1,3-butaneamine, 2-dimethylamino-2-hydroxypropane, diethyaminoethanol, N,N,N-tris(3-dimethylaminopropyl)amine, 2,4,6-tris(N,N,-dimethylaminomethyl)phenol, and heptamethylisobiguanide;

imidazoles such as imidazole, N-methylimidazole, 2-methylimidazole, 4-methylimidazole, N-ethylimidazole, 2-ethylimidazole, 4-ethylimidazole, N-butylimidazole, 2-butylimidazole, N-undecylimidazole, 2-undecylimidazole, N-phenylimidazole, 2-phenylimidazole, N-benzylimidazole, 2-benzylimidazole, 1-benzyl-2-methylimidazole, N-(2'-cyanoethyl)-2-methylimidazole, N-(2'-cycanoethyl)-2-undecylimidazole, N-(2'-cyanoethyl)-2-phenylimidazole, 3,3-bis-(2-ethyl-4-methylimidazolyl)methane, 2-mercaptoimidazole, 2-mercapto-N-methylimidazole, 2-mercaptobenzimidazole, 3-mercapto-4-methyl-4H-1,2,4-triazole, 5-mercapto-1-methyl-tetrazole, 2,5-dimercapto-1,3,4-thiadiazole, addition products of alkylimidazoles and isocyanuric acid and addition products of alkylimidazoles and formaldehyde; and amidines such as 1,8-diazabicyclo[5.4.0]undecene-7,1,5-diazabicyclo[4.3.0]nonene-5, and 6-dibutylamino-1,8-diazabicyclo[5.4.0]undecene-7.

(2) Complexes of Amines (1) and Borane or Boron Trifluoride (3) Phosphines

Trimethylphosphine, triethylphosphine, triisopropylphosphine, tri-n-butylphosphine, tri-n-hexylphosphine, tri-n-octylphosphine, tricyclohexylphosphine, triphenylphosphine, tribenzylphosphine, tris(2-methylphenyl)phosphine, tris(3-methylphenyl)phosphine, tris(4-methylphenyl)phosphine, tris(diethylamino)phosphine, tris(4-methylphenyl)phosphine, dimethylphenylphosphine, diethylphenylphosphine, dicyclohexylphenylphosphine, ethyldiphenylphosphine, diphenylcyclohexylphosphine, and chlorodiphenylphosphine.

(4) Quaternary Ammonium Salts

Tetramethylammonium chloride, tetramethylammonium bromide, tetramethylammonium acetate, tetraethylammonium chloride, tetraethylammonium bromide, tetraethylammonium acetate, tetra-n-butylammonium fluoride, tetra-n-butylammonium chloride, tetra-n-butylammonium bromide, tetra-n-butylammonium iodide, tetra-n-butylammonium acetate, tetra-n-butylammonium borohydride, tetra-n-butylammonium hexafluorophosphite, tetra-n-butylammonium hydrogensulfite, tetra-n-butylammonium tetrafluoroborate, tetra-n-butylammonium tetraphenylborate, tetra-n-butylammonium p-toluenesulfonate, tetra-n-hexylammonium chloride, tetra-n-hexylammonium bromide, tetra-n-hexylammonium acetate, tetra-n-octylammonium chloride, tetra-n-octylammonium bromide, tetra-n-octylammonium acetate, trimethyl-n-octylammonium chloride, trimethyldecylammonium chloride, trimethyldodecylammonium chloride, trimethylcetylammonium chloride, trimethyllaurylammonium chloride, trimethylbenzylammonium chloride, trimethylbenzylammonium bromide, triethyl-n-octylammonium chloride, triethylbenzylammonium chloride, triethylbenzylammonium bromide, tri-n-butyl-n-octylammonium chloride, tri-n-butylbenzylammonium fluoride, tri-n-butylbenzylammonium chloride, tri-n-butylbenzylammonium bromide, tri-n-butylbenzylammonium iodide, n-butyldimethylbenzylammonium chloride, n-octyldimethylbenzylammonium chloride, decyldimethylbenzylammonium chloride, dodecyldimethylbenzylammonium chloride, cetyldimethylbenzylammonium chloride, lauryldimethylbenzylammonium chloride, methyltriphenylammonium chloride, methyltribenzylammonium chloride, methyltriphenylammonium bromide, methyltribenzylammonium bromide, ethyltriphenylammonium chloride, ethyltribenzylammonium chloride, ethyltriphenylammonium bromide, ethyltribenzylammonium bromide, n-butyltriphenylammonium chloride, n-butyltribenzylammonium chloride, n-butyltriphenylammonium bromide, n-butyltribenzylammonium bromide, 1-methylpyridinium chloride, 1-methylpyridinium bromide, 1-ethylpyridinium chloride, 1-ethylpyridinium bromide, 1-n-butylpyridinium chloride, 1-n-butylpyridinium bromide, 1-n-hexylpyridinium chloride, 1-n-hexylpyridinium bromide, 1-n-octylpyridinium bromide, 1-n-dodecylpyridinium chloride, 1-n-dodecylpyridinium bromide, 1-n-cetylpyridinium chloride, 1-n-cetylpyridinium bromide, 1-phenylpyridinium chloride, 1-phenylpyridinium bromide, 1-benzylpyridinium chloride, 1-benzylpyridinium bromide, 1-methylpicolinium chloride, 1-methylpicolinium bromide, 1-ethylpicolinium chloride, 1-ethylpicolinium bromide, 1-n-butylpicolinium chloride, 1-n-butylpicolinium bromide, 1-n-hexylpicolinium chloride, 1-n-hexylpicolinium bromide, 1-n-octylpicolinium chloride, 1-n-octylpicolinium bromide, 1-n-dodecylpicolinium chloride, 1-n-dodecylpicolinium bromide, 1-n-cetylpicolinium chloride, 1-n-cetylpicolinium bromide, 1-phenylpicolinium chloride, 1-phenylpicolinium bromide, 1-benzylpicolinium chloride, and 1-benzylpicolinium bromide.

(5) Quaternary Phosphonium Salts

Tetramethylphosphonium chloride, tetramethylphosphonium bromide, tetraethylphosphonium chloride, tetraethylphosphonium bromide, tetra-n-butylphosphonium chloride, tetra-n-butylphosphonium bromide, tetra-n-butylphosphonium iodide, tetra-n-hexylphosphonium bromide, tetra-n-octylphosphonium bromide, methyltriphenylphosphonium bromide, methyltriphenylphosphonium iodide, ethyltriphenylphosphonium bromide, ethyltriphenylphosphonium iodide, n-butyltriphenylphosphonium bromide, n-butyltriphenylphosphonium iodide, n-hexyltriphenylphosphonium bromide, n-octyltriphenylphosphonium bromide, tetraphenylphosphonium bromide, tetrakishydroxymethylphosphonium chloride, tetrakishydroxymethylphosphonium bromide, tetrakishydroxyethylphosphonium chloride, and tetrakishydroxybutylphosphonium chloride.

(6) Tertiary Sulfonium Salts

Trimethylsulfonium bromide, triethylsulfonium bromide, tri-n-butylsulfonium chloride, tri-n-butylsulfonium bromide, tri-n-butylsulfonium iodide, tri-n-butylsulfonium tetrafluoroborate, tri-n-hexylsulfonium bromide, tri-n-octylsulfonium bromide, triphenylsulfonium chloride, triphenylsulfonium bromide, and triphenylsulfonium iodide.

(7) Secondary Iodonium Salts

Diphenyliodonium chloride, diphenyliodonium bromide, and diphenyliodonium iodide.

(8) Mineral Acids

Hydrochloric acid, sulfuric acid, nitric acid, phosphoric acid and carbonic acid, and half-esters of the mineral acids.

(9) Lewis Acids

Boron trifluoride and boron trifluoride etherate.

(10) Organic Acids

Organic acids and their semi esters.

(11) Silicic Acid Compounds and tetrafluoroboric Acid Compounds Silicic acid and tetrafluoroboric acid.

(12) Peroxides

Cumyl peroxyneodecanoate, diisopropyl peroxydicarbonate, diallyl peroxydicarbonate, di-n-propyl peroxydicarbonate, dimyristyl peroxydicarbonate, cumyl peroxyneohexanoate, t-hexyl peroxyneodecanoate, t-butyl peroxyneodecanoate, t-hexyl peroxyneohexanoate, t-butyl peroxyneohexanoate, 2,4-dichlorobenzoyl peroxide, benzoyl peroxide, dicumyl peroxide, di-t-butyl peroxide, cumene hydroperoxide, and tert-butyl hydroperoxide.

(13) Azo Compounds 2,2'-Azobis(4-methoxy-2,4-dimethylvaleronitrile), 2,2'-azobis(2-cyclopropylpropionitrile), 2,2'-azobis(2,4-dimethylvaleronitrile), 2,2'-azobisisobutylonitrile, 2,2'-azobis(2-methylbutylonitrile), 1,1'-azobis(cyclohexane-1-carbonitrile), 1-[(1-cyano-1-methyl)azo]formamide, 2-pneylazo-4-methoxy-2,4-dimethylvaleronitrile, 2,2'-azobis(2-methylpropane), and 2,2'-azobis(2,4,4-trimethylpentane).

(14) Condensates of Aldehyde and Ammonia Compound

Reaction product of acetaldehyde and ammonia, condensate of formaldehyde and p-toluidine, condensate of acetaldehyde and p-toluidine, reaction product of formaldehyde and aniline, reaction product of acetaldehyde and aniline, reaction product of butylaldehyde and aniline, reaction product of formaldehyde, acetaldehyde and aniline, reaction product of acetaldehyde, butylaldehyde and aniline, condensate of butylaldehyde and monobutylamine, reaction product of butylaldehyde and butylideneaniline, reaction product of heptaldehyde and aniline, reaction product of trichlotonylidenetetramine, condensate of α-ethyl-β-propylacrolein and aniline, and condensate of formaldehyde and alkylimidazole.

(15) Guanidine Compounds

Diphenylguanidine, phenyltolylguanidine, phenylxylylguanidine, tolylxylylguanidine, di-o-tolylguanidine, o-tolylguanide, diphenylguanidine phthalate, tetramethylguanidine, and di-o-tolylguanidine salt of dicatechol boric acid.

(16) Thiourea Compounds

Thiocarboanilide, di-o-tolylthiourea, ethylenethioure a, diethylthiourea, dibutylthiourea, dilaurylthiourea, trimethylthiourea, dimethylethylthiourea, and tetramethylthiourea.

(17) Thiazole Compounds

2-Mercaptobenzothiazole, dibenzothiazyl disulfide, cyclohexylamine salt of 2-mercaptobenzothiazole, 2-(2,4-dinitrophenylthio)benzothiazole, 2-(morpholinodithio)benzothiazole, 2-(2,6-dimethyl-4-morpholinothio)benzothiazole, N,N-diethylthiocarbamoyl-2-benzothiazolyl disulfide, 1,3-bis(2-benzothiazolylmercaptomethyl)urea, benzothiadiazylthio benzoate, 2-mercaptothiazoline, sodium salt of 2-mercaptobenzothiazole, zinc salt of 2-mercaptobenzothiazole, and complex of dibenzothiazyl disulfide and zinc chloride.

(18) Sulfenamide Compounds

N-cyclohexyl-2-benzothiazyl sulfenamide, N-t-butyl-2-benzothiazyl sulfenamide, N-t-oxtyl-2-benzothiazyl sulfenamide, N-oxydiethylene-2-benzothiazyl sulfenamide, N,N-diethyl-2-benzothiazyl sulfenamide, N,N-diisopropyl-2-benzothiazyl sulfenamide, and N,N-dicyclohexyl-2-benzothiazyl sulfenamide.

(19) Thiuram Compounds

Tetramethylthiuram monosulfide, tetraethylthiuram monosulfide, tetrabutylthiuram monosulfide, dipentamethylenethiuram monosulfide, tetramethylthiuram disulfide, tetraethylthiuram disulfide, tetrabutylthiuram disulfide, N,N'-dimethyl-N,N'-diphenylthiuram disulfide, N,N'-diethyl-N,N'-diphenylthiuram disulfide, dipentamethylenethiuram disulfide, dipentamethylenethiuram tetrasulfide, and cyclic thiuram.

(20) Salts of Dithiocarbamic Acid

Sodium dimethyldithiocarbamate, sodium diethyldithiocarbamate, sodium dibutyldithiocarbamate, sodium pentamethylenedithiocarbamate, sodium cyclohexylethyldithiocarbamate, potassium dimethyldithiocarbamate, lead dimethyldithiocarbamate, zinc dimethyldithiocarbamate, zinc diethyldithiocarbamate, zinc dibutyldithiocarbamate, zinc dibenzyldithiocarbamate, zinc pentamethylenedithiocarbamate, zinc dimethylpentamethylenedithiocarbamate, zinc ethylphenyldithiocarbamate, bismuth dimethyldithiocarbamate, cadmium diethyldithiocarbamate, cadmium pentamethylenedithiocarbamate, selenium dimethyldithiocarbamate, selenium diethyldithiocarbamate, tellurium dimethyldithiocarbamate, tellurium diethyldithiocarbamate, iron dimethyldithiocarbamate, copper dimethyldithiocarbamate, diethylammonium diethyldithiocarbamate, N,N-dicyclohexylammonium dibutyldithiocarbamate, piperidinium pentamethylenedithiocarbamate, cyclohexylethylammonium sodium cyclohexylethyldithiocarbamate, pipecolinium methylpentamethylenedithiocarbamate, and complex of zinc pentamethylenedithiocarbamate and piperidine.

(21) Salts of Xanthogenic Acid

Sodium isopropylxanthate, zinc isopropylxanthate, zinc butylxanthate, and disulfide dibutylxanthate.

(22) Esters of Acid phosphoric Acid

Mono- or dimethyl phosphate, mono- or diethyl phosphate, mono- or dipropyl phosphate, mono- or dibutyl phosphate, mono- or dihexyl phosphate, mono- or dioctyl phosphate, mono- or didecyl phosphate, mono- or didodecyl phosphate, mono- or diphenyl phosphate, mono- or dibenzyl phosphate, and mono- or didecanol phosphate.

The polymerization catalysts recited above are only illustrative and not limited thereto as long as a compound is effective for curing the composition by polymerization. These catalysts may be used alone or in combination of two or more. The addition amount of the catalyst is 0.0001 to 10.0 parts by weight, preferably 0.0005 to 5.0 parts by weight based on 100 parts by weight of the composition for optical materials (the alicyclic compound and the optional reactive compound and additive compound).

To improve the practical properties of the optical materials of the present invention, the composition may be cured by polymerization in the presence of a known additive such as antioxidants and ultraviolet light absorbers. It is effective to improve the adhesion or the releasability between the cured materials and a mold by adding a known external and/or internal adhesion improver if the cured material is easy to separate from the mold during polymerization, or by adding a known external or internal mold release improver if the cured material is difficult to release from the mold after polymerization.

After uniformly blended with the catalyst, the adhesion or mold release improver, the additive such as antioxidants, bluing agents, ultraviolet absorbers, and property improvers, the alicyclic compound alone or a composition comprising it is cast into a mold made of glass or metal, heated to allow the curing by polymerization to proceed, and then released from the mold to obtain the optical materials of the present invention.

Before casting into the mold, the alicyclic compound alone or a composition comprising it may be pre-polymerized partly or completely in the presence or absence of a catalyst with or without stirring at −100 to 160° C. for 0.1 to 480 h. Then, the optical materials are produced by following the casting into a mold and the curing by polymerization. The pre-polymerization is effective, in particular, if the composition for optical materials includes a solid component and is not easy to handle. The pre-polymerization is performed preferably at −10 to 120° C. for 0.1 to 240 h, more preferably at 0 to 100° C. for 0.1 to 120 h.

As described above, a composition prepared by blending the main starting material and the secondary starting material is cast into a mold and cured therein by polymerization to provide the optical materials of the present invention. The alicyclic compound, the reactive compound, the additive compound, the catalyst and the additive such as adhesion improvers, mold release improvers, antioxidants, bluing agents, ultraviolet absorbers and property improvers may be blended under stirring in a single container simultaneously or stepwise. Alternatively, a few of the starting materials are blended in separate containers and then blended together in the same container. The order or adding the starting materials and additives is not specifically limited. The mixing temperature and time are not critical as long as the materials are sufficiently mixed. An excessively high temperature and an excessively long mixing time unfavorably make the casting operation difficult because undesirable reaction between the materials and additives is induced to increase the viscosity. The mixing temperature is about −50 to 100° C., preferably −30 to 70° C., more preferably −5 to 50° C., The mixing time is 1 min to 12 h, preferably 5 min to 10 h, more preferably 5 min to 6 h. The degasification under reduced pressure prior to the mixing, during the mixing or after the mixing of the materials and additives is preferred to prevent the generation of bubbles during the subsequent casting step and curing step by polymerization. The degree of evacuation is about 0.1 to 700 mmHg, preferably 0.5 to 300 mmHg. To increase the quality of the optical materials of the invention, it is preferred to remove impurities by filtering the materials or additives, before or after mixing, through a filter having a pore size of about 0.05 to 3 μm. After casting the starting mixture into a glass or metal mold, the curing by polymerization is conducted using an electric furnace, a water bath or an oil bath. The curing time is 0.1 to 100 h, preferably 1 to 72 h. The curing temperature is −10 to 160° C., preferably 0 to 140° C. The polymerization is carried out by keeping the starting mixture at a given polymerization temperature for a given period of time while raising the temperature at 0.1 to 100° C./h, lowering the temperature at 0.1 to 100° C./b or using a combination thereof. After curing, it is preferred to anneal the optical material at 50 to 150° C. for 10 min to 5 h because the strain of the optical material can be removed. The optical material may be further subjected to surface treatment for improving dyeability, providing hard coating and imparting non-reflection, non-fogging or impact resistance properties.

The present invention will be described in more detail by reference to the following examples which should not be construed to limit the scope of the invention thereto. The refractive index (Nd) and Abbe's number (vd) of the lenses were measured at 25° C. using Abbe refractometer.

SYNTHESIS EXAMPLE 1

Into a reaction flask equipped with a thermometer and a calcium chloride drying tube, 381.4 g (2.0 mol) of toluenethiosulfenyl chloride and 1000 mL of chloroform were charged and cooled to −80° C. Stirring vigorously, a solution of 116.2 g (1.0 mol) of 1,4-dithiane-2,5-diene in 500 mL of chloroform was added dropwise. 1,4-Dithiane-2,5-diene was prepared by the method described in J. Am. Chem. Soc., 75, 2065 (1953). After the addition, the reaction was allowed to proceed at room temperature for 30 min. After adding a solution of 74.1 g (0.95 mol) of sodium sulfide in 500 mL of methanol, the reaction was allowed to further proceed at 50° C. for one hour. The reaction product was added with 1000 mL of water and 1000 mL of chloroform to collect the lower chloroform layer, followed by drying and evaporation. The residue was purified by distillation and silica gel column chromatography to obtain 45.2 g of the product.

The product was identified as 1,2:4,5-diepithio-3,6-dithiacyclohexane represented by the following formula 3:

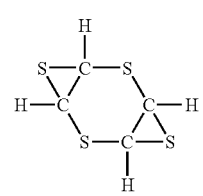

(3)

by elemental analysis, mass spectrometry and IR spectrometry.

Elemental Analysis

|  | Found | Calculated |
|---|---|---|
| C | 26.44% | 26.64% |
| H | 2.41% | 2.24% |
| S | 71.01% | 71.12% |

Mass Spectrum (EI)

| Found | Calculated |
|---|---|
| 180 | 180 |

Infrared Absorption Spectrum 620-630 cm$^{-1}$ (stretching vibration of epithioethylene linkage)

EXAMPLE 1

1,2:4,5-Diepithio-3,6-dithiacyclohexane (100 parts by weight) prepared in Synthesis Example 1 and 0.02 part by weight of N-methylimidazole (catalyst) were mixed to a uniform liquid, which was then filtered through a PTFE filter (0.5 μm pore size), cast into a mold for flat lens of 2.5 mm thick, and cured by polymerization in an oven by raising the temperature from 10° C. to 120° C. over 22 h to produce a lens. The obtained lens was excellent in heat resistance and physical properties, and showed an excellent transparency and surface condition. The refractive index was 1.78 and the Abbe's number was 30.

COMPARATIVE EXAMPLE 1

The procedure of Example 1 was repeated except for using 100 parts by weight of 1,2:6,7-diepithio-4-thiaheptane represented by the following formula 4:

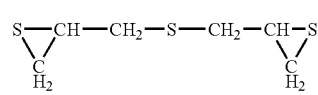

(4)

in place of 1,2:4,5-diepithio-3,6-dithiacyclohexane. The obtained lens had a refractive index of 1.71 and an Abbe's number of 36.

INDUSTRIAL APPLICABILITY

The alicyclic compound of the present invention alone or a composition for optical materials containing it is cured by polymerization to provide optical materials having a higher refractive index.

What is claimed is:

1. An alicyclic compound of five- or more membered ring structure, which has two or more epithioethylene linkages and/or epidithioethylene linkages in its ring structure and two or more sulfur atoms in its molecule, and which is selected from the group consisting of 1,2:4,5-diepithio-3-thiacyclohexane, 1,2:4,5-diepithio-3,6-dithiacyclohexane, 1,2:4,5-diepidithio-3,6-dithiacyclohexane, 1,2:4,5-diepithio-3,6,7-trithiacycloheptane, 1,2:5,6-diepithio-3,4,7,8-tetrathiacyclooctane, 1,2:5,6-diepidithio-3,4,7,8-tetrathiacyclooctane, 1,2:1,4:4,5-triepithio-3,6-dithiacyclohexane, 1,2:1,4:2,5:4,5-tetraepithio-3,6-dithiacyclohexane, and 1,2:1,4:2,5:4,5-tetraepidithio-3,6-dithiacyclohexane.

2. A composition for optical materials comprising the alicyclic compound as defined in claim 1.

3. The composition for optical materials according to claim 2, wherein a content of the alicyclic compound is 5 to 100% by weight based on the total amount of the composition for optical materials.

4. The composition for optical materials according to claim 3, further comprising a compound capable of reacting with the alicyclic compound.

5. The composition for optical materials according to claim 4, wherein the compound capable of reacting with the alicyclic compound is an episulfide compound having an epithioethyl group and/or an epidithioethyl group.

6. The composition for optical materials according to claim 2, further comprising a compound capable of reacting with the alicyclic compound.

7. The composition for optical materials according to claim 6, wherein the compound capable of reacting with the alicyclic compound is an episulfide compound having an epithioethyl group and/or an epidithioethyl group.

8. The composition for optical materials according to claim 7, wherein a content of the episulfide compound is 1 to 95 parts by weight based on 100 parts by weight of the alicyclic compound.

9. A method for producing optical materials, comprising a step of curing the alicyclic compound as defined in claim 1 by polymerization.

10. An optical material produced by the method according to claim 9.

11. A lens comprising the optical material according to claim 10.

12. A method for producing optical materials, comprising a step of curing the composition for optical materials as defined in claim 2 by polymerization.

* * * * *